(12) United States Patent
Freed et al.

(10) Patent No.: US 8,628,962 B2
(45) Date of Patent: Jan. 14, 2014

(54) DIFFERENTIATION OF STEM CELLS INTO DOPAMINERGIC CELLS

(75) Inventors: William J. Freed, Bowie, MD (US); Tandis Vazin, Walnut Creek, CA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 73 days.

(21) Appl. No.: 13/129,661

(22) PCT Filed: Nov. 18, 2009

(86) PCT No.: PCT/US2009/065007
§ 371 (c)(1),
(2), (4) Date: May 17, 2011

(87) PCT Pub. No.: WO2010/059738
PCT Pub. Date: May 27, 2010

(65) Prior Publication Data
US 2011/0236355 A1    Sep. 29, 2011

Related U.S. Application Data

(60) Provisional application No. 61/199,652, filed on Nov. 18, 2008.

(51) Int. Cl.
- *C12N 5/00* (2006.01)
- *C12N 5/02* (2006.01)
- *A01N 63/00* (2006.01)
- *A01N 65/00* (2009.01)

(52) U.S. Cl.
USPC .......... 435/377; 435/375; 435/384; 424/93.1; 424/93.7

(58) Field of Classification Search
None
See application file for complete search history.

(56) References Cited

FOREIGN PATENT DOCUMENTS

EP    1516924    3/2005

OTHER PUBLICATIONS

Itskovitz-Eldor, 2000, Molecular Medicine, 6:88-95.*
Storch Journal of Chemical Neuroanatomy, 2003, 26:133-142.*
Freed et al., "Gene Expression Profile of Neuronal Progenitor Cells Derived from hESCs: Activation of Chromosome 11p15.5 and Comparison to Human Dopaminergic Neurons," *PLoS One*, vol. 3, No. 1, e1422, 2008 (12 pages).
Marchionini et al., "Role of heparin binding growth factors in nigrostriatal dopamine system development and Parkinson's disease," *Brain Research*, vol. 1147, pp. 77-88, 2007.
Schulz et al., "Differentiation of Human Embryonic Stem Cells to Dopaminergic Neurons in Serum-Free Suspension Culture," *Stem Cells*, vol. 22, pp. 1218-1238, 2004.
Vazin et al., "Assessment of Stromal-Derived Inducing Activity in the Generation of Dopaminergic Neurons from Human Embryonic Stem Cells," *Stem Cells*, vol. 26, No. 6, pp. 1517-1525, 2008.
Vazin et al., "Dopaminergic Neurons derived from BG01V2, a variant of human embryonic stem cell line BG01," *Restor. Neurol. Neurosci.*, vol. 26, No. 6, pp. 447-458, 2008.
Vazin et al., "A Novel Combination of Factors, Termed SPIE, which Promotes Dopaminergic Neuron Differentiation from Human Embryonic Stem Cells," *PLoS One*, vol. 4, No. 8, e6606, 2009 (14 pages).
Yamazoe et al., "Collection of neural inducing factors from PA6 cells using heparin solution and their immobilization on plastic culture dishes for the induction of neurons from embryonic stem cells," *Biomaterials*, vol. 26, pp. 5746-5754, 2005.
Zeng et al., "Properties of Pluripotent Human Embryonic Stem Cells BG01 and BG02," *Stem Cells*, vol. 22, pp. 292-312, 2004.

* cited by examiner

*Primary Examiner* — Valarie Bertoglio
(74) *Attorney, Agent, or Firm* — Klarquist Sparkman, LLP

(57) ABSTRACT

Methods for differentiating stem cells are disclosed herein. These methods can be used to generate neurons, including, but not limited to, dopaminergic neurons. The disclosed methods include culturing stem cells in the absence of fibroblast growth factor-2 to generate embryoid bodies and culturing the embryoid bodies in the presence of an effective amount of at least one of stromal cell-derived factor 1, pleiotrophin, insulin-like growth factor 2, and ephrin B1 on an extracellular matrix for a period of time sufficient to produce dopaminergic neuronal cells. The differentiated cells can be used to study pharmaceutical agents that affect dopaminergic neurons and can be used in the treatment of neurodegenerative disorders such as Parkinson's disease.

22 Claims, 14 Drawing Sheets

FIG. 6A
FIG. 6B
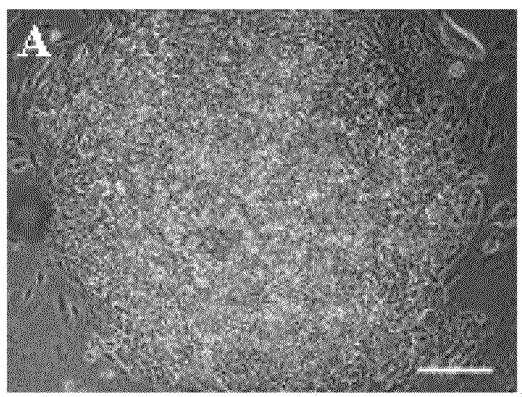 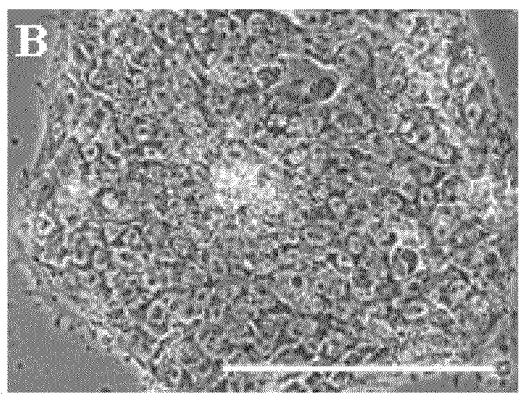
FIG. 6C
FIG. 6D
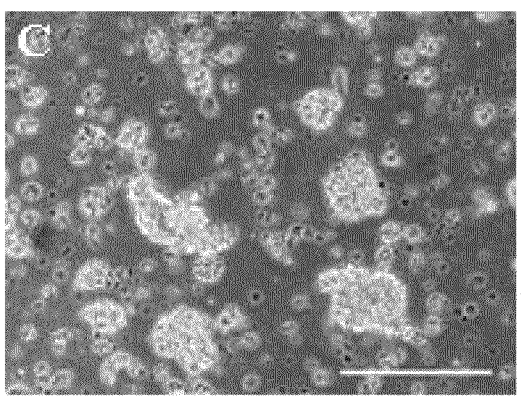 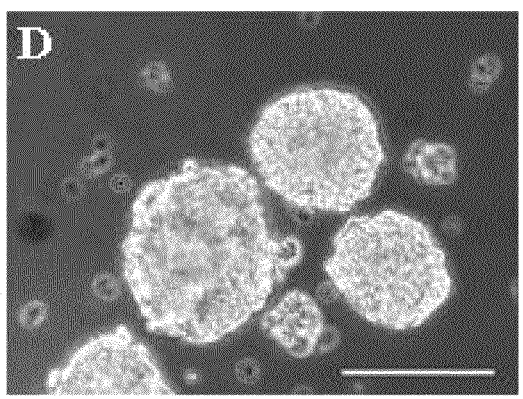
FIG. 6E
FIG. 6F
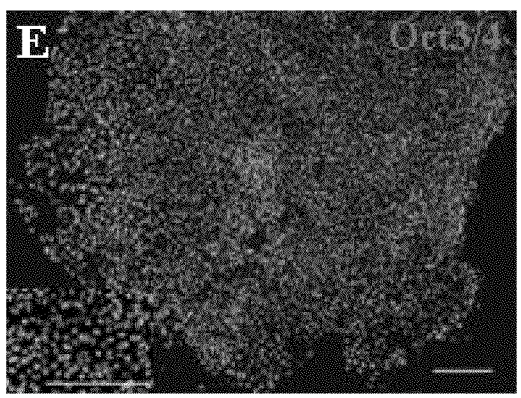 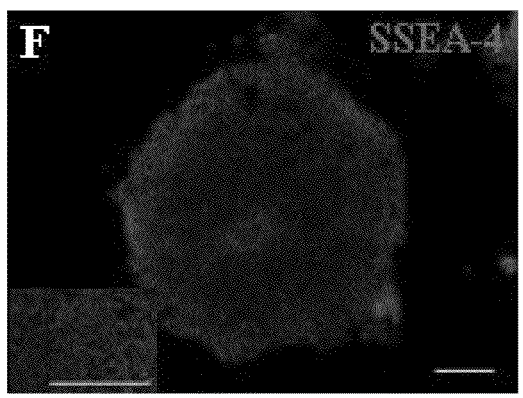

DIFFERENTIATION OF STEM CELLS INTO DOPAMINERGIC CELLS

CROSS REFERENCE TO RELATED APPLICATION APPLICATIONS

This is the §371 U.S. National Stage of International Application No. PCT/US2009/065007, filed Nov. 18, 2009, which was published in English under PCT Article 21(2), which in turn claims the benefit of U.S. Provisional Application No. 61/199,652, filed Nov. 18, 2008, which is incorporated by reference herein in its entirety.

FIELD

This invention relates to the field of methods for the in vitro production of differentiated cells from stem cells, such as the production of dopaminergic neuronal cells.

BACKGROUND

Neurons in the central and peripheral nervous systems degenerate as a normal function of human development and aging. Pathological neuron degeneration, however, is a serious condition seen in several neurological disorders. Neuronal degeneration can be specific or diffuse, and can lead to sensory, motor and cognitive impairments. Neurodegenerative disorders encompass a range of seriously debilitating conditions including Parkinson's disease (PD), amyotrophic lateral sclerosis (ALS, "Lou Gehrig's disease"), multiple sclerosis, Huntington's disease (HD), Alzheimer's disease, pantothenate kinase associated neurodegeneration (PKAN, formerly Hallervorden-Spatz syndrome), multiple system atrophy, diabetic retinopathy, multi-infarct dementia, macular degeneration, and the like. These conditions are characterized by a gradual but relentless worsening of the patient's condition over time. These disorders affect a large population of humans, especially older adults. Nevertheless, the understanding of these disorders is extremely limited and incomplete.

Many advances have been made in gaining a better understanding of PD, Alzheimer's disease and HD. The primary cause of cognitive dysfunction for all three disorders has been directly linked to neuron degeneration, usually in specific areas of the brain. PD is linked to degeneration of neurons in the substantia nigra, while Alzheimer's disease is in some part due to loss of pyramidal neurons in the limbic cortex (Braak, E. & Braak, H., 1999, In: V. E. Koliatsos & R. R. Ratan (eds.), *Cell Death and Diseases of the Nervous System*, Totowa, N.J.: Humana Press, pp. 497-508). HD's cognitive deficits are produced by degeneration of cells in the caudate nucleus of the striatum. However, although the symptoms and progression of these diseases are well characterized, the causes and triggers at onset are not well understood.

Thus, several strategies are being pursued to develop new therapies for neurodegenerative disorders, including PD. For PD, the techniques range from the use of dopaminotrophic factors (Takayama et al., *Nature Med.* 1:53-58, 1995) and viral vectors (Choi-Lundberg et al., *Science* 275:838-841, 1997) to the transplantation of primary xenogeneic tissue (Deacon et al., *Nature Med.* 3:350-353, 1997). Transplantation of dopaminergic neurons is a clinically promising experimental treatment in late stage PD. More than 200 patients have been transplanted worldwide (Olanow et al., *Trends Neurosci.* 19:102-109, 1996), and clinical improvement has been confirmed (Olanow et al., supra, and Wenning et al., *Ann. Neurol.* 42:95-107, 1997) and was correlated to good graft survival and innervation of the host striatum (Kordower et al., *N. Engl. J. Med.* 332:1118-1124, 1995). However, fetal nigral transplantation therapy generally requires human fetal tissue from at least 3-5 embryos to obtain a clinically reliable improvement in the patient. A different source of these neurons is clearly needed.

Dopaminergic neurons have been generated from murine CNS precursor cells (PCT Application No. PCT/US99/16825; Studer et al., *Nature Neurosci.* 1:290-295, 1998). These precursor-derived neurons are functional in vitro and in vivo and restore behavioral deficits in a rat model of PD. Even though the primary mesencephalic CNS stem cell culture can provide differentiated dopaminergic neurons suitable for use in cell therapy, the cell number provided by this method is limited. The percentage of differentiated dopaminergic neurons obtained from expanded mesencephalic precursors decreases as the cells are expanded more than about 10-100 fold. Mesencephalic precursors can generate only about 10% to 15% dopaminergic neurons (out of total cell number) after 10-100 fold expansion, and when the precursors are expanded 1000 fold, that number drops further, to only about 1%. Thus, a need clearly remains for alternate sources of these cells. In addition, there is a need for reliable methods for generating larger numbers of primate neurons.

SUMMARY

Methods for differentiating stem cells (such as embryonic stem cells (ESC), for example, primate ESC or human ESC) are disclosed herein. These methods can be used to generate neurons, including, but not limited to, dopaminergic (DA) neuronal cells. The disclosed methods include culturing stem cells (such as embryonic stem cells) in the absence of fibroblast growth factor (FGF)-2 to generate embryoid bodies (EB) and culturing the EBs in the presence of an effective amount of at least one of stromal cell-derived factor 1 (SDF-1/CXCL12), pleiotrophin (PTN), insulin-like growth factor 2 (IGF2), and ephrin B1 (EFNB1) on an extracellular matrix for a period of time sufficient to produce DA neuronal cells. In a particular embodiment, the EBs are cultured in the presence of all of SDF-1, PTN, IGF2, and EFNB1 for a period of time sufficient to produce DA neuronal cells (for example a period of time of about 2-50 days, such as about 7-35 days, about 10-24 days, for example at least about 7 days). In particular examples, the stem cells are human ESCs, such as BG01, BG02, or BG03 cells, or cells derived from BG01, BG02, or BG03 cells (for example, BG01V2 cells).

In some examples, the EBs are cultured in the presence of about 100 ng/ml SDF-1, about 100 ng/ml PTN, about 100 ng/ml IGF2, and about 200 ng/ml EFNB1. In additional examples, the EBs are cultured in the presence of an effective amount of heparin (such as about 1 ng/ml to 1 mg/ml, for example about 100 ng/ml) in addition to SDF-1, PTN, IGF2, and/or EFNB1.

In some examples, the EBs are cultured on an extracellular matrix that includes factors to improve attachment, growth, and/or differentiation of the EBs. In a particular example, the extracellular matrix includes poly-L-ornithine and laminin.

In one embodiment, the differentiated cells can be used in the treatment of neurodegenerative disorders. In some examples, the method includes producing dopaminergic neuronal cells using the methods provided herein and administering a therapeutically effect amount of the dopaminergic neuronal cells to a subject having a neurodegenerative disorder (for example, Parkinson's disease, Alzheimer's disease, or Huntington's disease). In particular examples, the DA neuronal cells are transplanted in the brain of a subject with a neurodegenerative disorder.

The foregoing and other features of the disclosure will become more apparent from the following detailed description, which proceeds with reference to the accompanying figures.

BRIEF DESCRIPTION OF THE DRAWINGS

FIG. 6A through F is a series of digital images showing phase contrast images of BG01V2 colonies maintained in feeder free cultures (A, B). Small clusters of BG01V2 cells cultured in low-attachment plates and incubated in suspension culture (C). EBs after 4 days in suspension culture (D). Immunostaining with stem cell markers Oct3/4 (E) and SSEA-4 (F) confirmed the undifferentiated state of the stem cells under feeder-free conditions. Scale bars=200 µm.

SEQUENCE LISTING

Figures 1A, 1B:
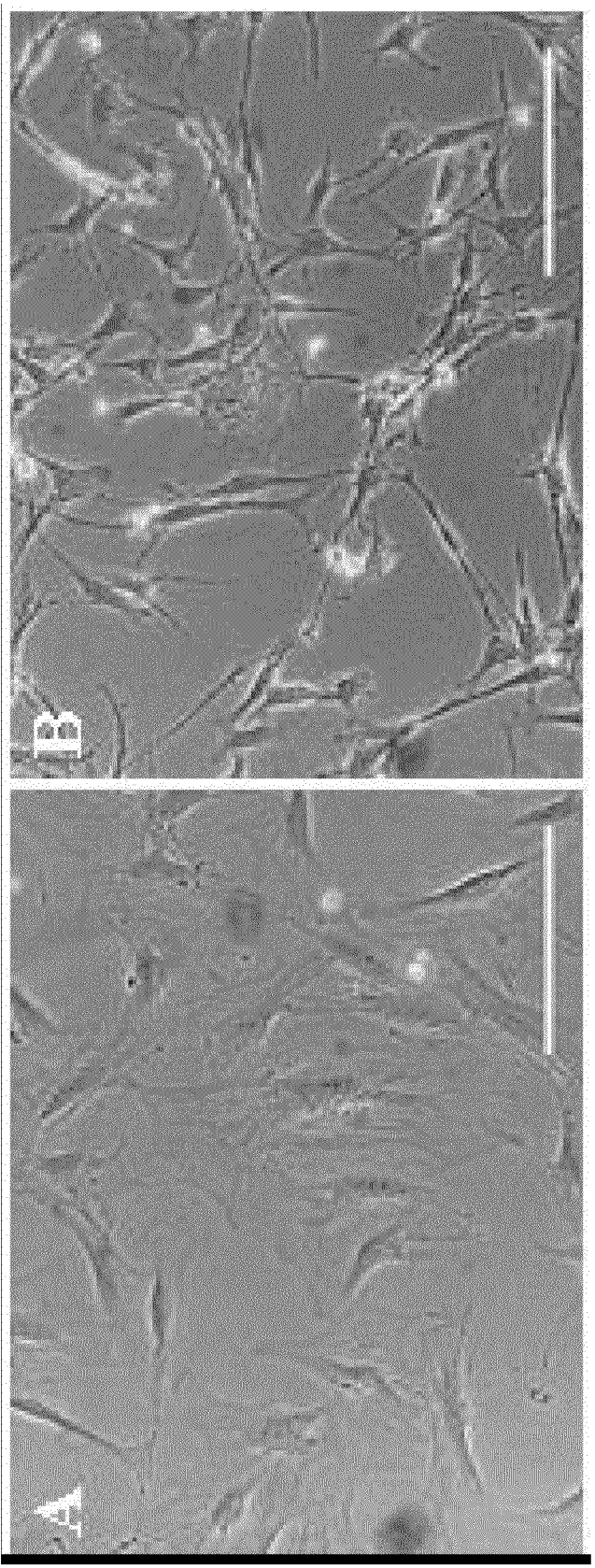
FIGS. 1A and B is a pair of digital images showing (A) PA6-DA cells morphology and (B) PA6-X cell morphology. Scale bars=200 µm.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1 and 2 are forward and reverse mouse IGF2 primers, respectively.

SEQ ID NOs: 3 and 4 are forward and reverse mouse PTN primers, respectively.

SEQ ID NOs: 5 and 6 are forward and reverse mouse CXCL12 primers, respectively.

SEQ ID NOs: 7 and 8 are forward and reverse mouse EFNB1 primers, respectively.

SEQ ID NOs: 9 and 10 are forward and reverse mouse IGFBP4 primers, respectively.

SEQ ID NOs: 11 and 12 are forward and reverse mouse retinol binding protein 1 (RBP1) primers, respectively.

SEQ ID NOs: 13 and 14 are forward and reverse mouse vascular cell adhesion molecule 1 (VCAM1) primers, respectively.

SEQ ID NOs: 15 and 16 are forward and reverse mouse Adamts5 primers, respectively.

SEQ ID NOs: 17 and 18 are forward and reverse mouse decorin (DCN) primers, respectively.

SEQ ID NOs: 19 and 20 are forward and reverse mouse collagen type 1 alpha 2 (COL1A2) primers, respectively.

SEQ ID NOs: 21 and 22 are forward and reverse human LIM homeobox transcription factor 1b (Lmx1b) primers, respectively.

SEQ ID NOs: 23 and 24 are forward and reverse human aromatic L-amino acid decarboxylase (AADC) primers, respectively.

SEQ ID NOs: 25 and 26 are forward and reverse human tyrosine hydroxylase (TH) primers, respectively.

SEQ ID NOs: 27 and 28 are forward and reverse human brain-derived neurotrophic factor receptor TrkB primers, respectively.

SEQ ID NOs: 29 and 30 are forward and reverse human engrailed 1 (En1) primers, respectively.

SEQ ID NOs: 31 and 32 are forward and reverse human paired-like homeodomain transcription factor 3 (Pitx3) primers, respectively.

SEQ ID NOs: 33 and 34 are forward and reverse human smoothened (Smo) primers, respectively.

SEQ ID NOs: 35 and 36 are forward and reverse human dopamine transporter (DAT) primers, respectively.

SEQ ID NOs: 37 and 38 are forward and reverse human c-RET primers, respectively.

SEQ ID NOs: 39 and 40 are forward and reverse human glial cell line derived neurotrophic factor family receptor alpha 1 (GFRA1) primers, respectively.

SEQ ID NOs: 41 and 42 are forward and reverse human glyceraldehyde-3-phosphate dehydrogenase (GAPDH) primers, respectively.

The Sequence Listing is submitted as an ASCII text file in the form of the file named Sequence_Listing.txt, which was created on May 9, 2011, and is 9,033 bytes, which is incorporated by reference herein.

DETAILED DESCRIPTION

There is great interest in the possibility of using stem cells, such as embryonic stem cells (ESC) to produce specific somatic cell types which might be used either in cellular therapy or as in vitro models of cell function. Dopaminergic neurons have use in treating Parkinson's disease (PD) and as in vitro models for testing drugs, such as agents for treating neurodegenerative disorders and agents for treating drug abuse. These neurons can also be used to study neuronal function in vitro.

The most commonly-used technique for producing high yields of DA neurons from ESC (referred to as stromal-derived inducing activity (SDIA)) requires a co-culture step, often using stromal cells such as the mouse PA6 cell line, human astrocytes, or other cell lines (e.g., Kawasaki et al., *Neuron* 28:31-40, 2000; Barberi et al., *Nature Biotechnol.* 21:1200-1207, 2003; Tang et al., *J. Clin. Invest.* 115:102-109, 2005; Buytaert-Hoefen et al., *Stem Cells* 22:669-674, 2004). Often, patterning factors including sonic hedgehog (SHH) and fibroblast growth factor 8 (FGF8) are employed, but these factors are effective only following an early induction step (e.g., Lee et al., *Nature Biotechnol.* 18:675-679, 2000; Lau et al., *Neuroreport* 17:975-979, 2006). However, for clinical translation to treat human subjects, all cell-based therapeutic agents would need to be free of animal-derived cells or materials because of concerns about possible transfer of pathogens or xenogens, which may trigger immune reactions in human subjects. Hence, identification of the molecular mechanisms involved in SDIA is needed in order to develop a chemically-defined environment for efficient dopaminergic induction.

The inventors carried out gene expression profiling of PA6 cells using DNA microarrays to reveal differential expression of genes coding for soluble factors with a potential role in the dopaminergic induction of hESC. In order to select the most relevant set of molecules, comparisons were made between the potent PA6 cell line and mouse embryonic fibroblasts (MEF), mouse kidney cell line MM55K, and sub-types of PA6 and MS5 lines that lack dopaminergic inducing activity. On the basis of the results of the comparative microarray analysis, a set of candidate genes was selected, including SDF-1, PTN, IGF2, Insulin-like growth factor binding protein 4 (IGFBP4), and EFNB1. The combination of SDF-1, PTN, IGF2, and EFNB1 (SPIE) was found to be most effective at inducing differentiation of ESCs to dopaminergic neurons.

I. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Absence: A condition in which a particular compound or component is not present. However, the term "absence" does not require an absolute lack of the indicated compound. In some examples, "absence" of a compound includes a medium wherein exogenous compound (for example, FGF-2) is not added, or medium that contains less than a particular amount of the compound (for example, less than about 25 pg/ml of FGF-2, such as less than about 15 pg/ml, less than about 10 pg/ml medium, less than about 5 pg/ml, or less than about 1 pg/ml). In another example, "absence" indicates that the compound (such as FGF-2) cannot be detected using a standard assay, such as an immunoassay (for example ELISA or bead-based assays) or mass spectrometry.

Administering: To provide or give a subject a substance or compound, such as dopaminergic neuronal cells, by any effective route. In some examples, dopaminergic neuronal cells are administered to a subject by transplantation, for example, by injecting the cells at a particular location or brain region (for example, the caudate nucleus, putamen, and/or substantia nigra).

Animal: Living multi-cellular vertebrate organisms, a category that includes, for example, mammals and birds. The term mammal includes both human and non-human mammals. Similarly, the term "subject" includes both human and veterinary subjects.

Central Nervous System (CNS): The part of the nervous system of an animal that contains a high concentration of cell bodies and synapses and is the main site of integration of nervous activity. In higher animals, the CNS generally refers to the brain and spinal cord.

Culturing or Cell Culture: Growth of a population of cells in a defined set of conditions (such as culture medium, extracellular matrix, temperature, and/or time of culture) in vitro. In some examples, a cell culture includes a substantially pure culture (for example, isolated embryonic stem cells). In additional examples a cell culture includes a mixed culture, such as co-culture of two or more types of cells (for example a culture of embryonic stem cells with a feeder layer). In further examples, a cell culture includes cells grown in contact with an extracellular matrix (such as an extracellular matrix including poly-L-ornithine and/or laminin).

Differentiation: The process whereby relatively unspecialized cells (e.g., embryonic cells) acquire specialized structural and/or functional features characteristic of mature cells. Similarly, "differentiate" refers to this process. Typically, during differentiation, cellular structure alters and tissue-specific proteins and properties appear. The term "differentiated neuronal cell" refers to cells expressing a nucleic acid or protein characteristic of the specific neuronal cell type, exhibiting synaptic vesicle release, or having an electrophysiological characteristic of a neuronal cells (e.g., sustained bursts of action potentials). A differentiated neuronal cell can be a dopaminergic cell.

Differentiation medium: A synthetic set of culture conditions with the nutrients necessary to support the growth or survival of cells, and which allows the differentiation of cells, such as stem cells.

Dopaminergic neurons/neuronal cells: Cells that produce the neurotransmitter dopamine. Typically, dopaminergic neurons are highly concentrated in the substantia nigra of the midbrain.

Dopamine, along with epinephrine, norepinephrine, and serotonin, belongs to a chemical family referred to "monoamines." Within the family of monoamines, epinephrine, norepinephrine, and dopamine are derived from the amino acid tyrosine and form a subfamily called the catecholamines. Frequently, tyrosine hydroxylase (TH), the rate-limiting enzyme for the biosynthesis of dopamine, is used as a marker to identify dopaminergic neurons. Other markers for dopaminergic neurons include aromatic-L-amino acid decarboxylase (AADC) and the dopamine transporter (DAT).

Effective amount or therapeutically effective amount: The amount of an agent sufficient to prevent, treat, reduce and/or ameliorate the symptoms and/or underlying causes of any disorder or disease, or the amount of an agent sufficient to produce a desired effect on a cell. In one embodiment, an "effective amount" is an amount sufficient to produce differentiation of at least some stem cells in a population to differentiate to a desired cell type, such as dopaminergic neurons. In one embodiment, a "therapeutically effective amount" is an amount sufficient to reduce or eliminate a symptom of a disease, such as PD. In another embodiment, a therapeutically effective amount is an amount sufficient to overcome the disease itself.

Embryoid bodies (EB): Stem cell aggregates generated when stem cells (for example, embryonic stem cells) are plated on a non-adhesive surface that prevents attachment and differentiation of the stem cells. Generally, embryoid bodies include an inner core of undifferentiated stem cells surrounded by primitive endoderm.

Embryonic Stem Cells (ES cells or ESC): Pluripotent cells isolated from the inner cell mass of the developing blastocyst, or the progeny of these cells. "ES cells" can be derived from any organism. ES cells can be derived from mammals, including mice, rats, rabbits, guinea pigs, goats, pigs, cows, non-human primates, and humans. In specific, non-limiting examples, the cells are human, non-human primate, or murine. Without being bound by theory, ES cells can generate a variety of the cells present in the body (bone, muscle, brain cells, etc.) provided they are exposed to conditions conducive to developing these cell types. Methods for producing murine ES cells can be found in U.S. Pat. No. 5,670,372, which is herein incorporated by reference. Methods for producing human ES cells can be found in U.S. Pat. No. 6,090,622, WO 00/70021 and WO 00/27995, which are herein incorporated by reference.

Ephrin B1 (EFNB1): A ligand of Eph-related tyrosine kinases that is highly conserved among rat, mouse, and human. The EFNB1 gene comprises 13.17 kb and 5 exons. The classic female craniofrontonasal syndrome (CFNS) phenotype is caused by heterozygous loss-of-function mutation in the EFNB1 gene.

An exemplary nucleic acid sequence for human EFNB1 can be found as GENBANK Accession No. NM_004429 (Oct. 29, 2008) and an exemplary amino acid sequence can be found as GENBANK Accession No. NP_004420 (Oct. 29, 2008), both herein incorporated by reference. In one example, EFNB1 includes a full-length wild-type (or native) sequence, as well as EFNB1 variants that retain the ability to promote differentiation of stem cells to dopaminergic neurons. In certain examples, EFNB1 has at least 80% sequence identity, for example at least 85%, 90%, 95%, or 98% sequence identity to one of the EFNB1 GENBANK sequences referenced above.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion" or "expanded." Typically, during an expansion phase, the cells do not differentiate to form mature cells.

Extracellular matrix: A substrate suitable for cell growth and/or attachment for in vitro cell culture, such as a tissue culture vessel (for example, a dish, plate, or multi-well plate). In some examples, the substrate includes a three-dimensional scaffold or matrix that supports the cells. In some examples, the substrate includes molecules that promote cell attachment, growth, differentiation, or other desirable cell properties. In particular examples, the molecules are embedded in or are present on the surface of the tissue culture vessel. In one example, the extracellular matrix includes poly-L-ornithine and/or laminin.

Feeder layer: Non-proliferating cells (e.g. irradiated cells) that can be used to support proliferation of cells, including cells obtained from diverse sources including normal as well as neoplastic tissues from humans and laboratory animals. Protocols for the production of feeder layers are known in the art, and are available on the internet, such as at the National Stem Cell Resource website, which is maintained by the American Type Culture Collection (ATCC, Manassas, Va.).

Fibroblast growth factor or FGF: Any suitable fibroblast growth factor, derived from any animal, and functional fragments thereof. A variety of FGFs are known and include, but are not limited to, FGF-1 (acidic fibroblast growth factor), FGF-2 (basic fibroblast growth factor, bFGF), FGF-3 (int-2), FGF-4 (hst/K-FGF), FGF-5, FGF-6, FGF-7, FGF-8, FGF-9 and FGF-98. "FGF" refers to a fibroblast growth factor protein such as FGF-1, FGF-2, FGF-3, FGF-4, FGF-5, FGF-6, FGF-7, FGF-8, FGF-9 or FGF-98, or a biologically active fragment or mutant thereof. The FGF can be from any animal species. In one embodiment, the FGF is mammalian FGF, including but not limited to, rodent, avian, canine, bovine, porcine, equine and human. The amino acid sequences and method for making many of the FGFs are well known in the art.

FGF-2 (also known as bFGF or bFGF-2), and other FGFs, can be made as described in U.S. Pat. No. 5,155,214. The recombinant bFGF-2, and other FGFs, can be purified to pharmaceutical quality (98% or greater purity) using the techniques described in detail in U.S. Pat. No. 4,956,455. It should be noted that human and murine FGF-2, FGF-4, FGF-8 and a variety of other FGFs, are commercially available.

An exemplary nucleic acid sequence for human FGF-2 can be found as GENBANK Accession No. NM_002006 (Nov. 1, 2009) and an exemplary amino acid sequence can be found as GENBANK Accession No. NP_001997 (Nov. 1, 2009), both herein incorporated by reference. In one example, FGF-2 includes a full-length wild-type (or native) sequence, as well as FGF-2 allelic variants that retain FGF-2 activity. In certain examples, FGF-2 has at least 80% sequence identity, for example at least 85%, 90%, 95%, or 98% sequence identity to one of the FGF-2 GENBANK sequences referenced above.

Growth factor: A substance that promotes cell growth, survival, and/or differentiation. Growth factors include molecules that function as growth stimulators (mitogens), molecules that function as growth inhibitors (e.g. negative growth factors), factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation.

Growth medium or expansion medium: A synthetic set of culture conditions with the nutrients necessary to support the growth (cell division/expansion) of a specific population of cells. In one embodiment, the cells are stem cells (for example, ES cells or EC cells). In this embodiment, the growth media is a stem cell growth medium that allows stem cells to proliferate. In another embodiment, the cells are neuronal precursor cells. In this embodiment, the expansion medium is a neuronal precursor cell expansion medium that allows neuronal precursors to proliferate.

Growth media generally include a carbon source, a nitrogen source and a buffer to maintain pH. In one embodiment, stem cell growth medium contains a minimal essential media, such as DMEM, supplemented with various nutrients to enhance stem cell growth. Additionally, the minimal essential media may be supplemented with additives such as horse, calf or fetal bovine serum.

Heparin: A glycosaminoglycan that is a polymer including variably sulfated disaccharide units. The most common disaccharide unit includes 2-O-sulfated iduronic acid and 6-O-sulfated, N-sulfated glucosamine. Heparan-sulfate glycosaminoglycans such as heparin are known to interact with several growth factors and modulate their biological activity. In some examples, EBs are cultured in the presence of heparin and at least one of SDF-1, PTN, IGF2, and EFNB1.

Insulin-like Growth Factor-2 (IGF-2): A protein hormone that shares structural similarity to insulin. In humans, the IGF2 gene is located on chromosome 11p15.5. IGF2 exerts its effects by binding to the IGF1 receptor. IGF2 may also bind to the IGF2 receptor. The major role of IGF2 is as a growth promoting hormone during gestation.

Exemplary nucleic acid sequences for human IGF2 can be found as GENBANK Accession Nos. NM_000612 (Oct. 12, 2008), NM_001007139 (Nov. 1, 2009), and NM_001127598 (Nov. 1, 2009) and exemplary amino acid sequences for human IGF2 can be found as GENBANK Accession Nos. NP_000603 (Oct. 12, 2008), NP_001007140 (Nov. 1, 2009), and NP_001121070 (Nov. 1, 2009); all of which are herein incorporated by reference. In one example, IGF2 includes a full-length wild-type (or native) sequence, as well as IGF2 variants that retain the ability to promote differentiation of stem cells to dopaminergic neurons. In certain examples, IGF2 has at least 80% sequence identity, for example at least 85%, 90%, 95%, or 98% sequence identity to one of the IGF2 GENBANK sequences referenced above.

Isolated: An "isolated" biological component (such as a nucleic acid, peptide or protein) has been substantially separated, produced apart from, or purified away from other biological components in the cell of the organism in which the component naturally occurs, for example, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. In some examples, an isolated cell includes a cell that has been substantially purified from other cell types.

Laminin: A major glycoprotein component of basement membranes. Laminin is a multidomain protein including three disulfide-linked polypeptides: A chain (MW 400 kDa), B1, and B2 chains (MW 180-200 kDa). It modulates cell attachment, spreading, growth, motility, and differentiation. Cell attachment to laminin is mediated by integrins, such as the $\alpha1\beta1$, $\alpha2\beta1$, $\alpha3\beta1$, $\alpha6\beta1$, $\alpha7\beta1$, and $\alpha6\beta4$ integrins. In some examples, an extracellular matrix for cell culture includes laminin, for example, to improve cell adhesion to the surface or other characteristics.

Neurological disorder: A disorder in the nervous system, including the central nervous system (CNS) and peripheral nervous system (PNS). Examples of neurological disorders include Parkinson's disease, Huntington's disease, Alzheimer's disease, severe seizure disorders including epilepsy, familial dysautonomia as well as injury or trauma to the nervous system, such as neurotoxic injury or disorders of mood and behavior such as addiction, schizophrenia and amyotrophic lateral sclerosis. Neuronal disorders also include Lewy body dementia, multiple sclerosis, epilepsy, cerebellar ataxia, progressive supranuclear palsy, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Niemann Pick, and other lipid storage and genetic brain diseases and/or schizophrenia Neurodegenerative disorder: An abnormality in the nervous system of a subject, such as a mammal, in which neuronal integrity is threatened. Without being bound by theory, neuronal integrity can be threatened when neuronal cells display decreased survival or when the neurons can no longer propagate a signal. Specific, non-limiting examples of a neurodegenerative disorder are Alzheimer's disease, pantothenate kinase associated neurodegeneration (PKAN), Parkinson's disease, Huntington's disease (Dexter et al., *Brain* 114: 1953-1975, 1991), HIV encephalopathy (Miszkziel et al., *Magnetic Res. Imag.* 15:1113-1119, 1997), and amyotrophic lateral sclerosis.

Alzheimer's disease manifests itself as pre-senile dementia. The disease is characterized by confusion, memory failure, disorientation, restlessness, speech disturbances, and hallucination in mammals (*Medical, Nursing, and Allied Health Dictionary*, 4th Ed., 1994, Editors: Anderson, Anderson, Glanze, St. Louis, Mosby).

Parkinson's disease is a slowly progressive, degenerative, neurologic disorder characterized by resting tremor, loss of postural reflexes, and muscle rigidity and weakness (*Medical, Nursing, and Allied Health Dictionary*, 4th Ed., 1994, Editors: Anderson, Anderson, Glanze, St. Louis, Mosby).

Amyotrophic lateral sclerosis is a degenerative disease of the motor neurons characterized by weakness and atrophy of the muscles of the hands, forearms and legs, spreading to involve most of the body and face (*Medical, Nursing, and Allied Health Dictionary*, 4th Ed., 1994, Editors: Anderson, Anderson, Glanze, St. Louis, Mosby).

Pantothenate kinase associated neurodegeneration (PKAN, also known as Hallervorden-Spatz syndrome) is an autosomal recessive neurodegenerative disorder associated with brain iron accumulation. Clinical features include extrapyramidal dysfunction, onset in childhood, and a relentlessly progressive course (Dooling et al., *Arch. Neurol.* 30:70-83, 1974). PKAN is a clinically heterogeneous group of disorders that includes classical disease with onset in the first two decades, dystonia, high globus pallidus iron with a characteristic radiographic appearance (Angelini et al., *J. Neurol.* 239:417-425, 1992), and often either pigmentary retinopathy or optic atrophy (Dooling et al., *Arch. Neurol.* 30:70-83, 1974; Swaiman et al., *Arch. Neurol* 48:1285-1293, 1991).

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the cells herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent or "drug": A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Pleiotrophin (PTN): Pleiotrophin (also known as neurite growth-promoting factor 1 (NEGF1), heparin affin regulatory peptide (HARP), heparin binding growth-associated molecule (HB-GAM)) is an 18-kDa growth factor that has a high affinity for heparin and heparin-like molecules. It is structurally related to midkine and retinoic acid induced heparin-binding protein. Pleiotrophin was initially recognized as a neurite outgrowth-promoting factor present in rat brain around birth. During embryonic and early postnatal development, pleiotrophin is expressed in the central and peripheral nervous system and also in several non-neural tissues, notably lung, kidney, gut and bone.

An exemplary nucleic acid sequence for human PTN is set forth as GENBANK Accession No. NM_002825 (Oct. 5, 2008), and an exemplary amino acid sequence for human PTN is set forth as GENBANK Accession No. NP_002816 (Oct. 5, 2008), both herein incorporated by reference. In one example, PTN includes a full-length wild-type (or native) sequence, as well as PTN variants that retain the ability to promote differentiation of stem cells to dopaminergic neurons. In certain examples, PTN has at least 80% sequence identity, for example at least 85%, 90%, 95%, or 98% sequence identity to one of the PTN GENBANK sequences referenced above.

Poly-L-ornithine: A polymer of the amino acid ornithine. Poly-L-ornithine is sometimes referred to as an "attachment factor." Poly-L-ornithine may also facilitate cell spreading, growth, motility, and/or differentiation. In some examples, an extracellular matrix includes poly-L-ornithine to improve cell adhesion to the surface or other characteristics.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those which are recombinantly or synthetically produced.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Primers: Short nucleic acids, for example DNA oligonucleotides 10 nucleotides or more in length, which are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Probes and primers as used in the present disclosure may, for example, include at least 10 nucleotides of the nucleic acid sequences that are shown to encode specific proteins. In order to enhance specificity, longer probes and primers may also be employed, such as probes and primers that comprise 15, 20, 30, 40, 50, 60, 70, 80, 90 or 100 consecutive nucleotides of the disclosed nucleic acid sequences. Methods for preparing and using probes and primers are described in the references, for example Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences; Innis et al. (1990) *PCR Protocols, A Guide to Methods and Applications*, Innis et al.

(Eds.), Academic Press, San Diego, Calif. PCR primer pairs can be derived from a known sequence, for example, by using computer programs intended for that purpose such as Primer (Version 0.5, 1991, Whitehead Institute for Biomedical Research, Cambridge, Mass.).

When referring to a probe or primer, the term "specific for" (a target sequence) indicates that the probe or primer hybridizes under highly stringent conditions substantially only to the target sequence in a given sample comprising the target sequence.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one coded for by a recombinant nucleic acid molecule.

Sonic hedgehog (Shh): Sonic hedgehog (Shh) is one of three mammalian homologs of the Drosophila hedgehog signaling molecule and is expressed at high levels in the notochord and floor plate of developing embryos. Shh is known to play a key role in neuronal tube patterning (Echerlard et al., Cell 75:1417-30, 1993), the development of limbs, somites, lungs and skin. Moreover, overexpression of Shh has been found in basal cell carcinoma. U.S. Pat. No. 6,277,820 discloses amino acid and nucleic acid sequences of Shh.

Stem cell: A cell that can generate a fully differentiated functional cell of more than one given cell type. The role of stem cells in vivo is to replace cells that are destroyed during the normal life of an animal. Generally, stem cells can divide without limit. After division, the stem cell may remain as a stem cell, become a precursor cell, or proceed to terminal differentiation. Although appearing morphologically unspecialized, the stem cell may be considered differentiated where the possibilities for further differentiation are limited. A precursor cell is a cell that can generate a fully differentiated functional cell of at least one given cell type. Generally, precursor cells can divide. After division, a precursor cell can remain a precursor cell, or may proceed to terminal differentiation. A "neuronal stem cell" is a stem cell that can be differentiated into neurons. In one embodiment, a neuronal stem cell gives rise to all of the types of neuronal cells (e.g. dopaminergic, adrenergic, and serotinergic neurons) but does not give rise to other cells such as glial cells. A "neuronal precursor cell" is a precursor cell of the nervous system.

Stromal cell-derived factor 1 (SDF-1): Also known as CXCL12. Stromal cell-derived factors 1-alpha and 1-beta are small cytokines that belong to the intercrine family. It is strongly chemotactic for lymphocytes and alters the electrophysiology of neurons. SDF-1 includes the alpha, beta, and gamma isoforms. In particular examples, SDF-1 is SDF-1 alpha isoform.

Exemplary nucleic acid sequences for human SDF-1 can be found as GENBANK Accession Nos. NM_000609 (Oct. 23, 2008), NM_199168 (Nov. 1, 2009), and NM_001033886 (Nov. 1, 2009), and exemplary amino acid sequences for human SDF-1 can be found as GENBANK Accession Nos. NP_000600 (Oct. 23, 2008), NP_954637 (Nov. 1, 2009), and NP_001029058 (Nov. 1, 2009); all of which are herein incorporated by reference. In one example, SDF-1 includes a full-length wild-type (or native) sequence, as well as SDF-1 variants that retain the ability to promote differentiation of stem cells to dopaminergic neurons. In certain examples, SDF-1 has at least 80% sequence identity, for example at least 85%, 90%, 95%, or 98% sequence identity to one of the SDF-1 GENBANK sequences referenced above.

Subject: Any mammal, such as humans, non-human primates, pigs, sheep, cows, rodents and the like which is to be the recipient of the particular treatment. In one embodiment, a subject is a human subject or a rodent subject (such as a mouse or rat).

Synapse: Highly specialized intercellular junctions between neurons and between neurons and effector cells across which a nerve impulse is conducted (synaptically active). Generally, the nerve impulse is conducted by the release from one neuron (presynaptic neuron) of a chemical transmitter (such as dopamine or serotonin) which diffuses across the narrow intercellular space to the other neuron or effector cell (post-synaptic neuron). Generally neurotransmitters mediate their effects by interacting with specific receptors incorporated in the post-synaptic cell. "Synaptically active" refers to cells (e.g., differentiated neurons) which receive and transmit action potentials characteristic of mature neurons.

Treating: A therapeutic intervention that ameliorates a sign or symptom of a disease or pathological condition related to a disease (such as a neurodegenerative disease, for example, Parkinson's disease). Treating can also induce remission or cure of a condition. Reducing a sign or symptom associated with a neurodegenerative disease (such as Parkinson's disease, Alzheimer's disease, or Huntington's disease) can be evidenced, for example, by a delayed onset of clinical symptoms of the disease, a reduction in severity of some or all clinical symptoms of the disease, a slower progression of the disease (for example by prolonging the life of a subject having the disease), a reduction in the number of relapses of the disease, an improvement in the overall health or well-being of the subject, or by other parameters well known in the art that are specific to the particular disease.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, GenBank Accession numbers, and other references mentioned herein are incorporated by reference in their entirety for all purposes. In case of conflict, the present specification, including explanations of terms, will control. In addition, the materials, methods, and examples are illustrative only and not intended to be limiting.

II. Differentiation of Stem Cells to Dopaminergic Cells

The methods and cells described herein are based on the discovery that stem cells (such as embryonic stem cells) can be differentiated to form neuronal cells, such as dopaminergic neuronal cells.

In several embodiments, the method includes culturing stem cells in the absence of FGF-2 to generate embryoid bodies (EB) and culturing the EBs in the presence of an effective amount of at least one of stromal cell-derived factor 1 (SDF-1), pleiotrophin (PTN), insulin-like growth factor 2 (IGF2), and ephrin B1 (EFNB1) on an extracellular matrix for a period of time sufficient to produce human DA neuronal cells. Disclosed herein are methods for generating neuronal cells from stem cells (such as embryonic stem cells, for example, human and non-human primate ES cells) using a multi-step method. These methods can be used to produce dopaminergic neurons.

Stem Cells

A stem cell is a cell that can generate a fully differentiated functional cell of more than one given cell type. Stem cells include embryonic stem (ES) cells (for example, primate ES cells, such as human ES cells), embryonal carcinoma (EC) cells (for example, human EC cells), neuronal stem cells, or neuronal precursor cells.

Embryonic stem cells can proliferate indefinitely in an undifferentiated state. Furthermore, ES cells are totipotent cells, meaning that they can generate all of the cells present in the body (bone, muscle, brain cells, etc.). ES cells have been isolated from the inner cell mass (ICM) of the developing murine blastocyst (Evans et al., *Nature* 292:154-156, 1981; Martin et al., *Proc. Natl. Acad. Sci.* 78:7634-7636, 1981; Robertson et al., *Nature* 323:445-448, 1986). Additionally, human cells with ES properties have been isolated from the inner blastocyst cell mass (Thomson et al., *Science* 282:1145-1147, 1998) and developing germ cells (Shamblott et al., *Proc. Natl. Acad. Sci. USA* 95:13726-13731, 1998), and human and non-human primate embryonic stem cells have been produced (see U.S. Pat. No. 6,200,806, which is incorporated by reference herein).

As disclosed in U.S. Pat. No. 6,200,806, ES cells can be produced from human and non-human primates. In one embodiment, primate ES cells that express SSEA-3; SSEA-4, TRA-1-60, and TRA-1-81 are isolated in "ES medium" (see U.S. Pat. No. 6,200,806). ES medium consists of 80% Dulbecco's modified Eagle's medium (DMEM; no pyruvate, high glucose formulation, e.g., from Gibco BRL), with 20% fetal bovine serum (FBS; e.g., from Hyclone), 0.1 mM β-mercaptoethanol (e.g., from Sigma-Aldrich), 1% non-essential amino acid stock (e.g., from Gibco BRL). Generally, primate ES cells are isolated on a confluent layer of murine embryonic fibroblast cells in the presence of ES cell medium. In one example, murine embryonic fibroblasts are obtained from 12 day old fetuses from outbred mice (such as CF1, available from SASCO), but other strains may be used as an alternative. Tissue culture dishes treated with 0.1% gelatin (type I; e.g., from Sigma-Aldrich) can be utilized. Distinguishing features of ES cells, as compared to the committed "multipotential" stem cells present in adults, include the capacity of ES cells to maintain an undifferentiated state indefinitely in culture, and the potential that ES cells have to develop into every different cell types. Unlike mouse ES cells, human ES (hES) cells do not express the stage-specific embryonic antigen SSEA-1, but express SSEA-4, which is another glycolipid cell surface antigen recognized by a specific monoclonal antibody (see, e.g., Amit et al., *Devel. Biol.* 227:271-278, 2000, For rhesus monkey embryos, adult female rhesus monkeys (greater than four years old) demonstrating normal ovarian cycles are observed daily for evidence of menstrual bleeding (day 1 of cycle=the day of onset of menses). Blood samples are drawn daily during the follicular phase starting from day 8 of the menstrual cycle, and serum concentrations of luteinizing hormone are determined by radioimmunoassay. The female is paired with a male rhesus monkey of proven fertility from day 9 of the menstrual cycle until 48 hours after the luteinizing hormone surge; ovulation is taken as the day following the luteinizing hormone surge. Expanded blastocysts are collected by non-surgical uterine flushing at six days after ovulation. This procedure generally results in the recovery of an average 0.4 to 0.6 viable embryos per rhesus monkey per month (Seshagiri et al., *Am J. Primatol.* 29:81-91, 1993).

For marmoset embryos, adult female marmosets (greater than two years of age) demonstrating regular ovarian cycles are maintained in family groups, with a fertile male and up to five progeny. Ovarian cycles are controlled by intramuscular injection of 0.75 g of the prostaglandin PGF2a analog cloprostenol (Estrumate®, Mobay Corp, Shawnee, Kans.) during the middle to late luteal phase. Blood samples are drawn on day 0 (immediately before cloprostenol injection), and on days 3, 7, 9, 11, and 13. Plasma progesterone concentrations are determined by ELISA. The day of ovulation is taken as the day preceding a plasma progesterone concentration of 10 ng/ml or more. At eight days after ovulation, expanded blastocysts are recovered by a non-surgical uterine flush procedure (Thomson et al., *J Med. Primatol.* 23:333-336, 1994). This procedure results in the average production of 1.0 viable embryos per marmoset per month.

The zona pellucida is removed from blastocysts, such as by brief exposure to pronase (e.g., from Sigma-Aldrich). For immunosurgery, blastocysts are exposed to a 1:50 dilution of rabbit anti-marmoset spleen cell antiserum (for marmoset blastocysts) or a 1:50 dilution of rabbit anti-rhesus monkey (for rhesus monkey blastocysts) in DMEM for 30 minutes, then washed for 5 minutes three times in DMEM, then exposed to a 1:5 dilution of Guinea pig complement (e.g., from Gibco) for 3 minutes. After two further washes in DMEM, lysed trophectoderm cells are removed from the intact inner cell mass (ICM) by gentle pipetting, and the ICM plated on inactivated (3000 rads gamma irradiation) mouse embryonic fibroblasts.

After 7-21 days, ICM-derived masses are removed from endoderm outgrowths with a micropipette with direct observation under a stereo microscope, exposed to 0.05% Trypsin-EDTA (e.g., from Gibco) supplemented with 1% chicken serum for 3-5 minutes and gently dissociated by gentle pipetting through a flame polished micropipette.

Dissociated cells are re-plated on embryonic feeder layers in fresh ES medium, and observed for colony formation. Colonies demonstrating ES-like morphology are individually selected, and split again as described above. The ES-like morphology is defined as compact colonies having a high nucleus to cytoplasm ratio and prominent nucleoli. Resulting ES cells are then routinely split by brief trypsinization or exposure to Dulbecco's Phosphate Buffered Saline (PBS, without calcium or magnesium and with 2 mM EDTA) every 1-2 weeks as the cultures become dense. Early passage cells are also frozen and stored in liquid nitrogen.

Cell lines may be karyotyped with a standard G-banding technique (such as by the Cytogenetics Laboratory of the University of Wisconsin State Hygiene Laboratory, which provides routine karyotyping services) and compared to published karyotypes for the primate species.

Isolation of ES cell lines from other primate species would follow a similar procedure, except that the rate of development to blastocyst can vary by a few days between species, and the rate of development of the cultured ICMs will vary between species. For example, six days after ovulation, rhesus monkey embryos are at the expanded blastocyst stage, whereas marmoset embryos do not reach the same stage until 7-8 days after ovulation. The rhesus ES cell lines can be obtained by splitting the ICM-derived cells for the first time at 7-16 days after immunosurgery; whereas the marmoset ES cells were derived with the initial split at 7-10 days after immunosurgery. Because other primates also vary in their developmental rate, the timing of embryo collection, and the timing of the initial ICM split, varies between primate species, but the same techniques and culture conditions will allow ES cell isolation (see U.S. Pat. No. 6,200,806, which is incorporated herein by reference for a complete discussion of primate ES cells and their production).

Human ES cell lines exist and can be used in the methods disclosed herein. Human ES cells can also be derived from preimplantation embryos from in vitro fertilized (IVF) embryos. Experiments on unused human IVF-produced embryos are allowed in many countries, such as Singapore and the United Kingdom, if the embryos are less than 14 days old. Only high quality embryos are suitable for ES isolation. Present defined culture conditions for culturing the one cell human embryo to the expanded blastocyst have been described (see Bongso et al., *Hum Reprod.* 4:706-713, 1989). Co-culturing of human embryos with human oviductal cells results in the production of high blastocyst quality. IVF-derived expanded human blastocysts grown in cellular co-culture, or in improved defined medium, allows isolation of human ES cells with the same procedures described above for non-human primates (see U.S. Pat. No. 6,200,806).

Any human or non-human primate ES cell can be utilized with the methods disclosed herein (see U.S. Pat. No. 6,200,806, which is incorporated by reference in its entirety). In some examples, the methods described herein utilize previously derived hES cell lines. One cell line suitable for differentiation to dopaminergic neurons by the disclosed methods is the BG01 cell line and derivatives of the BG01 cell line, such as BG01V, BG01V2, BG02, and BG03 cell lines (BresaGen; Athens, Ga.). See e.g., Zeng et al., *Stem Cells* 22:292-312, 2004; Schulz et al., *Stem Cells* 22:1218-1238, 2004; Zeng et al., *Restor. Neurol. Neurosci.* 22:421-428, 2004; Vazin et al., *Restor. Neurol. Neurosci.* 26:447-458, 2008. In a particular example, BG01V2 cells are used in the methods described herein to produce a population of cells including dopaminergic neuronal cells.

In some examples, hES cell lines include H1, H7, H9, hES1, SNUhES1, SNUhES3, SNUhES16, SA002, HE3, HSF6, EBS, CCE, and derivatives of these cell lines. One of skill in the art can select additional hES cell lines that can be used with the methods described herein to produce dopaminergic neuronal cells.

In other examples, mouse ES cells may also be utilized with the methods described herein. Mouse embryonic stem cells (mESCs) are pluripotent cells derived from the inner cell mass of day 3.5 blastocysts. They can be maintained in vitro for extended periods without loss of their capacity to contribute to all cell lineages when reimplanted back into a blastocyst. mESCs can also be differentiated into various cell types, including dopaminergic neuronal cells, in vitro. Methods of producing mESCs are well known to one of skill in the art (see, e.g., *Manipulating the Mouse Embryo A Laboratory Manual*, Second Edition, Cold Spring Harbor Laboratory Press (1994)). Mouse ES cell lines are well known to one of skill in the art. Exemplary mESCs include, but are not limited to, R1, E14.1, and B5 cell lines. One of skill in the art can select additional mES cell lines that can be used with the methods described herein to produce dopaminergic neuronal cells.

In other examples, teratoma or teratocarcinoma cells (for example, embryonal carcinoma (EC) cells) may be used in the methods described herein to produce dopaminergic neuronal cells. Exemplary human EC cell lines include GCT27, NCCIT, NCG.R3, TERA2, NTERA2, and derivatives of these cell lines. EC cell lines are available, for example, from the American Type Culture Collection (Manassas, Va.). One of skill in the art can select additional EC cell lines that can be used with the methods described herein to produce dopaminergic neuronal cells.

In additional examples, the methods described herein may be utilized with induced pluripotent stem (iPS) cells. These cells are pluripotent cells that have been reprogrammed to an embryonic-like state; iPS cells have been generated from mouse embryonic and adult fibroblasts; human fetal, newborn, and adult fibroblasts; and primate (rhesus macaque) adult fibroblasts. See e.g., Takahashi and Yamanaka, *Cell* 126:663-676, 2006; Okita et al., *Nature* 448:313-317, 2007; Wernig et al., *Nature* 448:318-324, 2007; Yu et al., *Science* 318:1917-1920, 2007; Takahashi et al., *Cell* 131:861-872, 2007; Liu et al., *Cell Stem Cell* 3:587-590, 2008. iPS cells are similar to ESCs in that they are capable of differentiation into multiple tissue types (including neurons and cardiomyocytes), formation of teratomas and embryoid bodies, and germline competency. Methods for producing iPS cells (for example, mouse or human iPS cells) are known in the art. See, e.g., Takahashi and Yamanaka, *Cell* 126:663-676, 2006; Yu et al., *Science* 318:1917-1920, 2007; Takahashi et al., *Cell* 131: 861-872, 2007; Liu et al., *Cell Stem Cell* 3:587-590, 2008. Exemplary iPS cell lines include iPS(IMR90), iPS(Foreskin), iPS-DF19-9, iPS-DF4-3, and iPS-DF6-9 cell lines. iPS cell lines are available, for example, from the WiCell International Stem Cell Bank (Madison, Wis.).

Expansion of Undifferentiated Stem Cells

The expansion of stem cells (for example, ES cells) prior to differentiation is not required to perform the method disclosed herein. However, the stem cells can be expanded prior to EB formation.

In some examples, undifferentiated stem cells are cultured in stem cell proliferation media to expand the number of cells. Without being bound by theory, it is believed that primate ES cells can be expanded at least about 1000 fold without losing pluripotency. In one embodiment, the ES cells are human ES cells such as BG01, BG02 or BG03, or derivatives of these cell lines. Alternatively, the ES cells can be H9.1 or H9.2 (Amit et al., *Dev. Biol.* 227:271-278, 2000; Thomson et al., *Science* 282:5391, 1998) or human embryonic germ cells (EG cells) (Shamblott et al., *Proc. Natl. Acad. Sci. USA* 95:13726-13731, 1998).

In some embodiments, the stem cells are cultured in a stem cell growth medium which generally includes a carbon source, a nitrogen source and a buffer to maintain pH. In one embodiment, the stem cell growth medium is ES growth medium, which includes a minimal essential medium, such as Dulbecco's Modified Eagle's Medium (DMEM), supplemented with various nutrients to enhance ES cell growth. Additionally, the minimal essential medium may be supplemented with additives such as horse, calf or fetal bovine serum (for example, from between about 10% by volume to about 20% by volume or about 15% by volume) and may be supplemented with nonessential amino acids, L-glutamine, and antibiotics (such as streptomycin, penicillin, and combinations thereof). In some examples, FGF-2 may also be included in the media. ES growth media is commercially available, for example as KO-DMEM (e.g., Invitrogen, Catalog No. 10829-018).

Other methods and media for obtaining and culturing stem cells are known and are suitable for use (Evans et al., *Nature* 292:154-156, 1981; Martin et al., *Proc. Natl. Acad. Sci. USA* 78:7634-7636, 1981; Robertson et al., *Nature* 323:445-448, 1986; Doetschman et al., *Nature* 330:576-578, 1987; Thomas et al., *Cell* 51:503-512, 1987; Thomson et al., *Science* 282: 1145-1147, 1998; and Shamblott et al., *Proc. Natl. Acad. Sci.*

*USA* 95:13726-13731, 1998). The disclosures of these references are incorporated by reference herein.

In one specific, non-limiting example, the stem cells are cultured on plates which prevent differentiation of the stem cells. Suitable plates include those such as gelatin coated tissue culture plates, or plates which include a feeder cell layer.

"Feeder cells" or "feeders" are terms used to describe cells of one tissue type that are co-cultured with cells of a second tissue type, to provide an environment in which the cells of the second tissue type can grow. The feeder cells are optionally from a different species as the cells they are supporting. For example, certain types of stem cells can be supported by primary cultures of mouse embryonic fibroblasts, immortalized mouse embryonic fibroblasts, as described in U.S. Pat. No. 6,642,048. In co-culture with stem cells, feeder cells are typically inactivated by irradiation or treatment with an anti-mitotic agent such as mitomycin c, to prevent them from outgrowing the cells they are supporting. Feeder layers of use include a fibroblast feeder cell layer, such as a murine or a human fibroblast feeder layer. In one example, the feeder layer is mouse embryonic cell line (STO-1) or primary mouse embryonic fibroblasts, both treated with ultra-violet light or an anti-proliferative drug such as mitomycin C. In other examples, the feeder layer is a mouse kidney cell line (for example, MM55K cells), or mouse stromal cells that do not promote differentiation (for example, PA6-X or MS5 cells). Supportive adult human feeder cells are also exemplified by culture-expanded human bone marrow stromal cells (hMSCs) of passage 2 (p2) to p5, including hMSCs from multiple donors, which supported the growth of the H1 hES cell line under a serum-free condition (see published PCT Application No. WO 04/044158A2).

In other examples, feeder-free cultures of the stem cells are maintained and expanded on plates coated with fibronectin (e.g. about 1-100 µg/mlfibronectin, such as about 10-50 µg/ml, or about 20 µg/ml fibronectin) in medium conditioned by feeder cells, such as MEF conditioned medium. In particular examples, the conditioned medium is collected from the feeder cells daily, filtered, and used to feed the stem cells. In some examples, the conditioned medium is supplemented with FGF-2 (such as about 10-20 ng/ml FGF-2, for example about 12-18 ng/ml or about 16 ng/ml FGF-2).

In one embodiment, the stem cells are cultured in the presence of FGF-2, a growth factor that prevents differentiation of stem cells. In one example, the cells are grown on a feeder layer in the presence of about 1 to about 10 ng/ml of FGF-2. In several additional examples, the medium includes about 3 to about 7 ng/ml of FGF-2, or about 4 to about 5 ng/ml of FGF-2. In one embodiment, the stem cells are cultured for about 4 days to about 8 days. In another embodiment, the stem cells are cultured for about 5 days to about 7 days. The stem cells are cultured at temperature between about 35° C. and about 40° C., or at about 37° C. under an atmosphere which contains oxygen and between from about 1% to about 10%, or from about 1% to 5% $CO_2$, or about 5% $CO_2$. In one embodiment, the media is changed about every 1 to 2 days (see U.S. Pat. No. 5,670,372, herein incorporated by reference).

Generation of Embryoid Bodies (EB)

In one embodiment, embryoid bodies are generated from stem cells in suspension culture. Briefly, to form EBs, clusters of stem cells are disengaged from the tissue culture plates. Methods for disengaging cells from tissue culture plates are known and include the use of enzymes, such as trypsin or papain, and/or methyl ion chelators such as EDTA or EGTA, or commercially available preparations (e.g. see published PCT Application No. WO 00/27995). In other examples, cells are disengaged from the tissue culture plate mechanically, for example, by scraping and/or pipetting. The EBs can be generated in the absence of FGF-2. For example, the EBs can be generated in a medium wherein exogenous FGF-2 is not added, or in medium that contains less than about 25 pg/ml of FGF-2 (such as less than about 15 pg/ml, less than about 10 pg/ml medium, less than about 5 pg/ml, or less than about 1 pg/ml of medium). The media can be any media wherein FGF-2 cannot be detected using a standard assay, such as an immunoassay (for example ELISA or bead-based assays) or mass spectrometry.

The formation of EBs is well known in the art (see for example Conley et al., *Fetal Diagnosis and Therapy* 19:218-223, 2004; U.S. Pat. No. 6,602,711). Generally, EBs are generated by re-plating expanded stem cells into dishes, such as bacterial dishes, where they do not form aggregates. Tissue culture plates specifically designed for inhibiting cell attachment may also be used (e.g., ultra-low attachment plates, Corning, Lowell, Mass.). Generally, the stem cells disengage from the tissue culture plates in clusters (e.g., aggregates of 10 or more stem cells, typically 50 or more cells). The clusters of stem cells are then dissociated to obtain a population of cells which includes a majority of (e.g., between about 50% and about 70%, or between about 75% and about 90%, or between about 80% and about 100%) individual cells. Methods for dissociating clusters of cells are likewise known. One method for dissociating cells includes mechanically separating the cells, for example, by repeatedly aspirating a cell culture with a pipette. In one embodiment, the stem cells are in an exponential growth phase at the time of dissociation to avoid spontaneous differentiation that tends to occur in an overgrown culture.

The dissociated stem cells are then cultured in a medium, such as stem cell medium, by re-plating at a density of about $1 \times 10^5$ to about $10 \times 10^5$ cells per milliliter (cells/ml), such as about $2 \times 10^5$ cells/ml. In one embodiment, the cells are incubated from about 1 day to about 10 days, or about 2 to about 7 days, or for about 2 to 4 days, to produce EBs. In one embodiment, the medium is changed every 1 to 2 days (see Martin et al., *Proc. Natl. Acad. Sci.* 72:1441-1445, 1975; U.S. Pat. No. 5,014,268, herein incorporated by reference).

Generation of Neuronal Cells, Such as Dopaminergic Cells

EBs are then differentiated into neuronal cells (for example, dopaminergic neuronal cells) by culturing the EBs in the presence of an effective amount of at least one of stromal cell-derived factor 1 (SDF-1), pleiotrophin (PTN), insulin-like growth factor 2 (IGF2), and ephrin B1 (EFNB1) on an extracellular matrix for a sufficient period of time to produce human dopaminergic neuronal cells.

In one embodiment, the EBs are cultured in the presence of an effective amount of at least two or at least three of SDF-1, PTN, IGF2, and EFNB1. In a further embodiment, the method includes culturing the EBs in the presence of an effective amount of all of SDF-1, PTN, IGF2, and EFNB1. In several examples, the EBs are produced from human embryonic stem cells, for example, BG01, BG02 or BG03 cells, or are derived from BG01, BG02 or BG03 cells. In a particular example, the human embryonic stem cells are BG01V2 cells.

In one example, the method includes culturing the EBs in the presence of about 10 ng/ml to about 1 µg/ml of SDF-1, such as culturing the EBs in about 100 ng/ml of SDF-1. In another example, the method includes culturing the EBs in the presence of about 10 ng/ml to about 1 µg/ml of PTN, such as culturing the EBs in about 100 ng/ml of PTN. In a further example, the method includes culturing the EBs in the presence of about 10 ng/ml to about 1 µg/ml of IGF2, such as in about 100 ng/ml of IGF2. In yet another example, the method includes culturing the EBs in the presence of about 20 ng/ml to about 2 µg/ml of EFNB1, such as in about 200 ng/ml of EFNB1. In some examples, EFNB1 is an EFNB1 cluster, such as an EFNB1 multimer (for example, a dimer or tetramer). In a particular example, EFNB1 is an EFNB1 dimer, such as a disulfide-linked homodimer.

In a particular example, the EBs are cultured in the presence of about 100 ng/ml SDF-1, about 100 ng/ml PTN, about 100 ng/ml IGF2, and about 200 ng/ml EFNB1. In particular examples, "about" refers to amounts of the indicated factors that are within at least 10 ng/ml of the indicated amount (for example, within 10 ng/ml, 5 ng/ml, 2 ng/ml or 1 ng/ml of the indicated amount). The "SPIE" factors are commercially available (such as recombinant mouse or human proteins), for example from R&D Systems (Minneapolis, Minn.), Sigma-Aldrich (St. Louis, Mo.), Cell Sciences (Canton, Mass.), or MP Biomedicals (Solon, Ohio).

In some examples, the one or more factors are added to the stem cell culture medium (e.g., DMEM supplemented with Knockout serum replacement, L-glutamine, nonessential amino acids, antibiotics (such as penicillin-streptomycin), and β-mercaptoethanol). In some examples, the stem cell culture medium is a medium wherein exogenous FGF-2 is not added, or is a medium that contains less than about 25 pg/ml of FGF-2 (such as less than about 15 pg/ml, less than about 10 pg/ml medium, less than about 5 pg/ml, or less than about 1 pg/ml of medium). The medium can be any medium wherein FGF-2 cannot be detected using a standard assay, such as an immunoassay (for example ELISA or bead-based assays) or mass spectrometry.

The EBs are cultured in the presence of the factors described above on an extracellular matrix. The extracellular matrix includes a substrate suitable for cell growth and/or attachment for in vitro cell culture, such as a tissue culture vessel (for example, a dish, plate, or multi-well plate). In some examples, the substrate includes a three-dimensional scaffold or matrix that supports the cells (for example, a scaffold or gel including polyaminde matrix, cellulose acetate, poly-glycerolco-sebacate acrylate elastomers, fibrin or other mixtures (such as synthetic hydrogels, for example, HYDROMATRIX™ or MAXGEL™; BD Biosciences)). In some examples, the substrate includes molecules that promote cell attachment, growth, differentiation, or other desirable cell properties. In particular examples, the molecules are embedded in or are present on the surface of the tissue culture vessel. In some examples, the extracellular matrix includes molecules that promote attachment, such as poly-L-ornithine and/or laminin.

In one example, the EBs are cultured on a tissue culture plate precoated with poly-L-ornithine (e.g., 100 µg/ml poly-L-ornithine solution) and laminin (e.g., 20 µg/ml laminin solution). Tissue culture plates that are precoated with poly-L-ornithine and laminin are commercially available (e.g., BD Biosciences, Franklin Lakes, N.J.). In other examples, the extracellular matrix can include poly-D-lysine, poly-L-lysine, poly-L-ornithine, laminin, MATRIGEL™ (BD Biosciences, Franklin Lakes, N.J.), collagen, fibronectin, fibrin, or a combination of two or more thereof.

In further examples, the EBs are cultured in the presence of heparin (such as about 1 µg/ml to 1 mg/ml, for example about 100 µg/ml) in addition to the presence of SDF-1, PTN, IGF2, and/or EFNB1.

The EBs are incubated in the medium containing at least one of SDF-1, PTN, IGF2, and EFNB1 (such as one, two, three, or all of SDF-1, PTN, IGF2, and EFNB1) for a period of time sufficient to produce DA neuronal cells, such as between about 2 to about 50 days (for example, about 7 to 35 days, about 10 to 24 days, or about 14 to 21 days) at a temperature between about 35° C. and about 40° C. (such as about 37° C.). In some examples, the EBs are incubated in the medium containing at least one of SDF-1, PTN, IGF2, and EFNB1 (such as one, two, three, or all of SDF-1, PTN, IGF2, and EFNB1) for at least about 7 days (for example, at least about 10 days, at least about 14 days, at least about 16 days, at least about 18 days, at least about 21 days, at least about 28 days, at least about 35 days, at least about 45 days, at least about 50 days, or more) at a temperature between about 35° C. and about 40° C. (such as about 37° C.). The medium is changed about every 2-5 days, such as about every two, three, four, or five days. In some examples, a portion of the cell culture medium (such as about one-third or one-half of the medium) is replaced with fresh medium containing SDF-1, PTN, IGF2, and/or EFNB1. In one example, the cells are incubated at about 37° C. under between about 1% and 10% $CO_2$ atmosphere, or between about 5% and 10% $CO_2$ or under about 5% $CO_2$.

III. Characterization of Differentiated Stem Cells

The cells resulting from differentiation of stem cells using the methods described herein can be characterized by methods known in the art, including assessing cell morphology, gene expression, and cellular activity. In some examples, cells produced by differentiation of stem cells using the methods described herein are neuronal cells, such as dopaminergic neuronal cells.

Neuronal cells can be identified by their morphology, including the presence of neuritic processes. Neuronal cells are also identified by expression of neuronal markers, including, but not limited to microtubule-associated protein-2 (MAP-2), Noggin, nestin, β-III tubulin, neurofilament proteins (for example, neurofilament light, medium, or heavy proteins), synapsin, synaptophysin, and growth-associated protein 43. Other suitable neuronal markers can be selected by one of skill in the art.

In additional examples, the differentiated stem cells are dopaminergic neuronal cells. DA neuronal cells can be identified by their morphology, such as fusiform or multipolar cells (see e.g., Berger et al, *Neuroscience* 7:193-205, 1982; Grace and Onn *J. Neurosci.* 9:3463-3481, 1989). DA neuronal cell morphology can be identified by one of skill in the art. DA neuronal cells are also identified by expression of DA neuron markers, including, but not limited to the enzymes of the dopamine synthetic pathway (e.g., TH and AADC (also known as DOPA decarboxylase)) and the dopamine transporter (DAT). DA neuronal cells also express midbrain neuronal markers, such as Lmx1b, Pitx3, Ent and receptors such as GFR1, c-RET, TrkB, and Smo. Additional markers for DA neuronal cells can include forkhead box A1 (FOXA1), forkhead box A2 (FOXA2), IGF2, MSX1, NK2 homeobox 2 (NKX2-2), NK6 homeobox 1 (NKX6-1), orthodenticle homeobox 2 (OTX2), SRY (sex determining region Y)-box 1, SRY (sex determining region Y)-box 2 wingless-type, MMTV integration site family member 1 (Wnt1), and aldehyde dehydrogenase 1 family, member A1 (ALDH1A1). Other suitable DA neuronal markers can be selected by one of skill in the art.

In some examples, the dopaminergic cells express TH and/or other DA neuronal cell markers. In several examples, at least about 30%, at least about 40%, at least about 50%, at least about 60%, at least about 70%, at least about 80%, or at least about 90% express TH. In other examples, at least 20%, such as about 30%, 40%, 50%, 60% or more of the cells produce dopamine.

Methods of detecting expression of particular markers in a cell or cell population are well known in the art. In some examples, gene expression is assessed by measuring the amount of a nucleic acid (such as mRNA or cDNA) present in a sample, such as a differentiated stem cell. Methods of detecting a target nucleic acid molecule (such as RNA or DNA, for example mRNA or cDNA) in a sample are well known in the art. For example, nucleic acid amplification methods (with the appropriate probes and primers), as well as nucleic acid arrays (containing the appropriate probes), can be used. For example, the level of gene expression can be determined or even quantified utilizing methods well known in the art, such as Northern blots, RNase protection assays, nucleic acid arrays, reverse transcription-PCR, quantitative PCR (such as quantitative real-time PCR or TaqMan® assays), dot blot assays, in-situ hybridization, or combinations thereof. Gene expression can also be assessed by determining the amount of a protein present in a sample, such as a differentiated stem cell. Methods of detecting a protein in a sample are well known in the art. For example, immunoassays (for example, Western blotting or ELISA) and immunocytology (for example, immunohistochemistry or flow cytometry) methods can be used.

In additional examples, neuronal cells (such as DA neuronal cells) produced by the methods described herein are identified by assessing cellular activity, for example by electrophysiology. Electrophysiological methods are well known in the art and include voltage clamp recording and patch clamp recording. One of skill in the art can recognize electrophysiological activity of DA neuronal cells (for example, action potentials, particular potassium currents, and inhibition of firing by dopamine). See e.g., Silva et al., *J. Neurosci.* 64:262-272, 1990; Pitts et al., *Synapse* 6:309-320, 1990; Washio et al., *Neurosci. Res.* 34:91-101, 1999; Lin and Lipski, *J. Neurophysiol.* 85:1336-1339, 2001. In some examples, the DA neuronal cells exhibit action potentials (such as multiple action potentials) or spontaneous postsynaptic currents. In other examples, the DA neuronal cells exhibit voltage-gated currents (such as sodium and/or potassium currents) and currents in response to neurotransmitters (such as GABA and/or glutamate). In additional examples, the DA neuronal cells may exhibit a hyperpolarization-activated inward current (h-current or $I_h$; see, e.g., Silva et al., *J. Neurophysiol.* 64:262-272, 1990; Mercuri et al., *Euro. J. Neurosci.* 7:462-469, 1995; Lin and Lipski, *J. Neurophysiol.* 85:1336-1339, 2001). In some examples, the DA neuronal cells may form synapses.

IV. Exemplary Uses of the Differentiated Cells

The present methods can be employed to produce neuronal cells in order to deliver the cells, or molecules expressed by these cells, to the brain of a subject for diagnosis, treatment or prevention of disorders or diseases of the CNS, brain, and/or spinal cord. These disorders can be neurologic or psychiatric disorders. These disorders or diseases include brain diseases such as Alzheimer's disease, Parkinson's disease, Lewy body dementia, multiple sclerosis, epilepsy, cerebellar ataxia, progressive supranuclear palsy, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Niemann Pick, and other lipid storage and genetic brain diseases and/or schizophrenia. The method can also be employed in subjects suffering from or at risk for nerve damage from cerebrovascular disorders such as stroke in the brain or spinal cord, from CNS infections including meningitis and HIV, from tumors of the brain and spinal cord, or from a prior disease. The method can also be employed to deliver agents to counter CNS disorders resulting from ordinary aging (e.g., insomnia or loss of the general chemical sense), brain injury, or spinal cord injury.

The cells can be used in the treatment of Parkinson's disease (PD). The principal therapeutic target in the brain for PD is the caudate nucleus and putamen. Another therapeutic target in the brain for PD is the substantia nigra which extends forward over the dorsal surface of the basis peduncle from the rostral border of the pons toward the subthalamic nucleus. Other therapeutic target areas include the locus ceruleus which is located in the rostral pons region and the ventral tegmental area which is located dorsomedial to the substantia nigra.

After the differentiated neuronal cells (such as dopaminergic neuronal cells) are produced according to the methods described above, the cells are suspended in a physiologically compatible carrier (pharmaceutically acceptable carrier). The carrier can be any carrier compatible with the other ingredients of the formulation and not deleterious to the recipient thereof. Those of skill in the art are familiar with physiologically compatible carriers. Examples of suitable carriers include cell culture medium (e.g., Eagle's minimal essential media), phosphate buffered saline, and Hank's balanced salt solution +/−glucose (HBSS). In one embodiment, supporting cells, such as glia or astrocytes, can be added. These cells can be from the same species as the neuronal cells, or from a different species. Thus, in one embodiment, human stem cells (for example, human ES cells) are differentiated to human neuronal cells, and administered to the subject in conjunction with human glia or astrocytes. In another embodiment, the human neuronal cells are administered with murine astrocytes or glial cells to the subject.

The volume of cell suspension administered to a subject will vary depending on the site of implantation, treatment goal and amount of cells in solution. Typically the amount of cells administered to a subject will be a therapeutically effective amount. For example, where the treatment is for Parkinson's disease, transplantation of a therapeutically effective amount of cells will typically produce a reduction in the amount and/or severity of the symptoms associated with that disorder, e.g., rigidity, akinesia and gait disorder.

In some examples, at least about 100,000 dopaminergic neuronal ells are administered to a PD patient (such as at least about 200,000 cells, at least about 500,000 cells, at least about 750,000 cells, at least about 1 million cells, at least about 2 million cells, at least about 3 million cells, at least about 4 million cells, at least about 5 million cells, or more). In one example, a severe PD patient needs at least about 100,000 surviving dopamine cells per grafted site to have a substantial beneficial effect from the transplantation. As cell survival may be low in brain tissue transplantation in general (e.g., about 5-10%), in some examples at least about 1 million cells are administered, such as from about 1 million to about 5 million dopaminergic neuronal cells.

In one embodiment, the cells are administered to the subject's brain. The cells may be implanted within the parenchyma of the brain, in the space containing cerebrospinal fluids, such as the sub-arachnoid space or ventricles, or extaneurally. Thus, in one example, the cells are transplanted to regions of the subject which are not within the central nervous system or peripheral nervous system, such as the celiac ganglion or sciatic nerve. In another embodiment, the cells are transplanted into the central nervous system, which includes all structures within the dura mater.

Typically, the neuronal cells are administered by injection into the brain of the subject, for example into the caudate nucleus, putamen, substantia nigra, locus ceruleus, or ventral tegmental area. Injections can generally be made with a sterilized syringe having an 18-21 gauge needle. Although the exact size needle will depend on the species being treated, the needle should not be bigger than 1 mm diameter in any species. Those of skill in the art are familiar with techniques for administering cells to the brain of a subject.

In additional examples, the dopaminergic neuronal cells produced by the methods disclosed herein are administered to the subject in combination with one or more additional anti-Parkinson's disease agents. For instance, in some examples the additional anti-Parkinson's disease agent is levodopa (L-DOPA), carbidopa, a dopamine agonist (for example, bromocriptine, pergolide, pramipexole, or ropinirole), a catecholamine-O-methyltransferase inhibitor (for example, entacapone or tolcapone), amantadine, on an anticholinergic agent (for example, benztropine or trihexyphenidyl). Appropriate dosages and modes of administration of these and other additional anti-Parkinson's disease agents are known to one of skill in the art.

Cells produced by the methods disclosed herein can also be used in to screen test compounds (such as pharmaceutical agents) to select for agents that affect specific cell types, such as agents that affect neuronal cells. The cells can be used to study pharmaceutical agents that affect dopaminergic cells, or affect the expression of TH or Msx-1.

The test compound can be any compound of interest, including chemical compounds, small molecules, polypeptides, growth factors, cytokines, or other biological agents (for example antibodies). In several examples, a panel of potential chemotherapeutic agents, or a panel of potential neurotrophic agents are screened. In other embodiments a panel of polypeptide variants is screened.

Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386-390, 1992; Markland et al., *Gene* 109:13-19, 1991), a peptide library (U.S. Pat. No. 5,264,563); a peptidomimetic library (Blondelle et al., *Trends Anal Chem.* 14:83-92, 1995); a nucleic acid library (O'Connell et al., *Proc. Natl. Acad. Sci., USA* 93:5883-5887, 1996; Tuerk and Gold, *Science* 249:505-510, 1990; Gold et al., *Ann. Rev. Biochem.* 64:763-797, 1995); an oligosaccharide library (York et al., *Carb. Res.* 285:99-128, 1996; Liang et al., *Science* 274:1520-1522, 1996; Ding et al., *Adv. Expt. Med. Biol.* 376:261-269, 1995); a lipoprotein library (de Kruif et al., *FEBS Lett.* 3 99:232-236, 1996); a glycoprotein or glycolipid library (Karaoglu et al., *J. Cell Biol.* 130:567-577, 1995); or a chemical library containing, for example, drugs or other pharmaceutical agents (Gordon et al., *J. Med. Chem.* 37.1385-1401, 1994; Ecker and Crooke, *BioTechnology* 13:351-360, 1995). Polynucleotides can be particularly useful as agents that can alter a function of stem cells (such as, but not limited to ES cells) and precursor cells because nucleic acid molecules having binding specificity for cellular targets, including cellular polypeptides, exist naturally, and because synthetic molecules having such specificity can be readily prepared and identified (see, for example, U.S. Pat. No. 5,750,342).

In one embodiment, for a high throughput format, embryoid bodies or DA neuronal cells produced by the methods described herein can be introduced into wells of a multiwell plate or of a glass slide or microchip, and can be contacted with the test agent. Generally, the cells are organized in an array, particularly an addressable array, such that robotics conveniently can be used for manipulating the cells and solutions and for monitoring the stem or precursor cells, particularly with respect to the function being examined. An advantage of using a high throughput format is that a number of test agents can be examined in parallel, and, if desired, control reactions also can be run under identical conditions as the test conditions. As such, the methods disclosed herein provide a means to screen one, a few, or a large number of test agents in order to identify an agent that can alter a function of cells, for example, an agent that increases the number of cells differentiated to DA neuronal cells, or that increases survival of the differentiated dopaminergic neuronal cells.

In some examples, the cells are contacted with one or more test compounds for an amount of time sufficient to affect cell differentiation, survival, or gene expression. In one example, EBs produced by the methods described herein are contacted with SDF-1, PTN, IGF2, EFNB1, and one or more test compounds.

Cell survival can be assessed by methods known in the art, for example, by counting the number of cells present in the culture or dye-based assays for live cells (such as trypan blue, calcein AM, or ethidium homodimer dye assays). An increase in the number of cells or the number of live cells indicates that the test compound increases cell survival. Cell differentiation can be assessed by the methods described in Section III (above), including determining nucleic acid or protein levels of neuronal or dopaminergic cell markers, such as TH and/or Msx-1. An increase in expression of differentiated cell markers indicates that the test compound promotes or increases cell differentiation to dopaminergic neuronal cells.

The disclosure is illustrated by the following non-limiting examples:

EXAMPLES

Example 1

Materials and Methods

Cell Lines:

Mitotically inactivated MEF feeder layers (Chemicon, Temecula, Calif.) were cultured in cell culture dishes coated with 0.1% gelatin (Chemicon, Temecula, Calif.) with high-glucose Dulbecco's Modified Eagle's Medium (DMEM) (Gibco, Gaithersburg, Md.) supplemented with 10% fetal bovine serum (Atlanta Biologicals, Atlanta, Ga.) and 50 U/ml Penn-Strep. The MM55K mouse kidney cell line was purchased from American Type Culture Collection (ATCC, Manassas, Va.) and cultured with high-glucose DMEM containing 10% fetal bovine serum and 50 U/ml Penn-Strep. The PA6 mouse stromal cell line was obtained from Riken BioResource Center Cell Bank (Tsukuba, Japan). MS5 cells were provided by Dr. Caruz (University of Jaen, Spain). The stromal cell lines were cultured in α-minimum essential medium (Gibco) supplemented with 10% fetal bovine serum and 50 U/ml Penn-Strep. Sub-culturing of these cell lines was accomplished by trypsinization using 0.5-1 ml 0.05% trypsin-EDTA (Gibco) for 2-3 mM hESC lines used were BG01V2, BG02, and BG03, derived by BresaGen (Athens, Ga.). The BG01V2 hESC cell line is a variant of the hESC line BG01 (Vazin et al., *Restor. Neurol. Neurosci.* 26:447-458, 2008).

Mitotically inactivated MEFs were used as feeder cells to maintain BG01V2 in an undifferentiated state. The hESC culture medium consisted of Dulbecco's Modified Eagle Medium/nutrient mixture (1:1), supplemented with 10% Knockout serum replacement, 2 mM L-glutamine, 1 mM nonessential amino acid, 4 ng/ml bFGF (Invitrogen), 50 U/ml Penn-Strep (Gibco), and 0.1 mM β-mercaptoethanol (Chemicon). The culture media was changed daily with routine passage of hESC on fresh MEF layers carried out once a week. hESC colonies were isolated from the MEF feeder layers with 1 mg/ml collagenase type IV ((Invitrogen) treatment for approximately 1 hr. Feeder-free cultures of BG01V2 were grown on human fibronectin, 20 μg/ml, (BD Biosciences, Bedford, Mass.) in MEF conditioned medium (MEF-CM). MEF-CM was collected daily, filtered and supplemented with an additional 16 ng/ml of bFGF before feeding hESC. MEF cells were used for 8-10 days for CM collection. The CM was also frozen for storage at −20° C. up to one month and thawed for later use.

Co-Culture of BG01V2 with Feeder Cell Lines:

For co-culture experiments, the cell lines were grown to confluence in 6-well tissue culture plates in their respective growth media as previously described. Media was replaced with hESC differentiation medium comprised of Glasgow Minimum Essential Medium (GMEM) supplemented with 10% knockout serum replacement, 0.1 mM nonessential amino acids (Gibco), 1 mM sodium pyruvate (Sigma-Aldrich, St. Louis, Mo.) and 0.1 mM β-mercaptoethanol (Chemicon). MEFs and stromal cells were cultured in 0.1% gelatin and collagen type-I coated plates, respectively. The PA6 subtype PA6-X exhibited rapid cell division and a lack of contact inhibition of growth. Upon confluency, PA6-X feeder layers retracted and detached from the plates. To avoid detachment, cells were inactivated with 10 μg/ml mitomycin-c (Sigma) for one hr followed by three washes with fresh medium and permitted to recover overnight. BG01V2 colonies were dissociated from the MEF feeder layer by enzymatic treatment and added to the feeders at a density of 50-100 small colonies corresponding to 5000-10,000 cells/cm$^2$. The culture medium was changed on day four and every other day thereafter. The hESC were allowed to grow and differentiate on the feeder layers for 12 days.

Immunocytochemistry:

Cultures were fixed in 4% paraformaldehyde in PBS and then incubated with the primary antibodies in blocking buffer (PBS containing 5% goat serum, 2% BSA, and 0.2% Triton X-100) at room temperature for 2 hr.

The following primary antibodies were used: mouse anti-Oct 3/4 (1:50; Santa Cruz Biotechnology, Santa Cruz, Calif.), rabbit anti-TH (1:1000; Pel-Freez, Rogers, Ark.), mouse anti-a-smooth muscle actin (1:500), mouse anti-vimentin (1:500; both from Sigma), rabbit anti-β III-tubulin (1:2000; Promega, Madison, Wis.), mouse anti-nestin (1:50; R&D Systems, Minneapolis, Minn.), rabbit anti-GFAP (1:2000; Dako, Carpinteria, Calif.), mouse anti-MAP-2 (1:500, BD Biosciences, San Jose, Calif.), and rabbit anti-MAP-2 (1:1000; Chemicon). Cultures were incubated with fluorescent-labeled secondary antibodies [Alexa 488 (green) or Alexa 568 (red)-labeled goat IgG; 1:1000; Molecular Probes (Invitrogen)] in PBS with 1% BSA for 1 hour at room temperature. The cells were rinsed three times for 5 min in PBS. Negative controls studies were obtained by substituting the primary antibodies with non-immune mouse and rabbit IgG (1:100; Santa Cruz Biotechnology) and pre-absorption of the Oct3/4 primary antibody with its antigenic peptide (0.2 mg/ml of N-terminal Oct3/4 of human origin; Santa Cruz Biotechnology). To ensure the specificity of the polyclonal TH antibody, a monoclonal anti-TH antibody recognizing an epitope in the N-terminus (1:100; Sigma) was used. Cell morphology and intracellular localization were carefully examined to confirm expression of markers β-III-tubulin, MAP-2, GFAP, and nestin. Images were obtained using a Carl Zeiss Axiovert 200M microscope.

Statistical significance of the overall differences in numbers of colonies expressing various markers among the experimental groups was tested by analysis of variance (ANOVA) followed by Tukey-Kramer multiple comparisons test (GraphPad Software Inc., San Diego, Calif., USA). Differences were considered significant at $P<0.05$.

RNA Extraction and Expression Microarrays:

For total RNA extraction, about $5 \times 10^6$ cells from each of the five cell lines were seeded onto 100 mm dishes. After 2 days the cells were washed two times with PBS, collected by scraping and centrifuged. RNA-STAT 60 (Tel-Test Inc.) was used to isolate the RNA following manufacturer's instructions. RNAs derived from all the feeder cell lines were reverse-transcribed, labeled, and analyzed using the Illumina microarray platform (Sentrix Mouse-8 Expression BeadChip). Arrays were processed according to the manufacturer's instructions.

Microarray Data Analysis:

Z-score transformation method was used to compare the gene expression levels between the five cell lines independent of the original hybridization intensities (Cheadle et al., *J. Mol. Diagn.* 5:73-81, 2003). To obtain fold-like change in gene expression, Z scores were converted to Z ratios and used for significance analysis to select differentially expressed genes. Statistical analysis was based on an increase of a Z-ratio change of at least 3.0 and $P<0.05$.

Functional information in relation to the gene products and gene expression patterns were obtained from the literature or from the following databases: OMIM (available on the World Wide Web at ncbi.nlm nih gov/sites/entrez?db=omim), Source (available on the World Wide Web at genome-www5.stanford.edu/cgi-bin/source/sourceBatchSearch), Cell Migration Consortium (available on the World Wide Web at cmckb.cellmigration.org), Allen Brain Atlas (ABA) (available on the World Wide Web at www.brain-map.org). Significantly altered genes (Z ratio≥3.0) were categorized using the platform gene ontology FatiGO (Fast Assignment and Transference of Information using Gene Ontology, available on the World Wide Web at fatigo.org) with respect to gene function including biological process and molecular function (Al-Shahrour et al., *Bioinformatics* 20:578-580, 2004).

Reverse Transcriptase-Polymerase Chain Reaction (RT-PCR):

Complementary DNA for the polymerase chain reaction (PCR) was reverse transcribed from total RNA isolated from each feeder cell line. cDNA was synthesized from 2 μg RNA using an oligo dT primer and 1 μA MMLV (Promega, reverse transcription kit) in a 24 μA reaction according to the manufacturer's recommendations. The cycling parameters were as follows: 65° C., 2 mM; 42° C., 60 mM; 72° C., 10 mM 100 units of MMLV-RT was added 10 mM after the reaction was brought to 42° C. The PCR reaction components for detection of the candidate genes were as follows, 1 μl cDNA in 50 μl of PCR mix containing 5×PCR buffer, 5 μl of 15 mM MgCl$_2$, 2 μl of 10 mM deoxyribonucleoside triphosphate (dNTP), 0.5 μl each of 100 μM primers, and 5 units of GoTaq® DNA polymerase (all from Promega). The thermal cycling parameters were as follows: primary denaturation, three minutes at 94° C.; 35 cycles of denaturation for 1 mM at 94° C.; annealing for 1 min at 55° C.; extension for 1 min at 72° C. and final extension for 7 minutes at 72° C.

Equal amounts of RNA were tested in PCR reactions under the same conditions to verify the absence of amplification of genomic DNA. The housekeeping gene, glyceraldehyde-3-phosphate dehydrogenase (GAPDH), was amplified as an internal control in gene expression analysis.

Primer sequences used in the current work were determined from the PrimerBank website (available on the World Wide Web at pga.mgh.harvard.edu/primerbank/) and synthesized by Invitrogen. The primer sequences are presented in Tables 1 and 2.

TABLE 1

Mouse PCR Primer Sets

| Gene | Primer Bank ID | Forward | Reverse |
|---|---|---|---|
| IGF2 | 6754310a1 | GTGCTGCATCGCTGCTTAC (SEQ ID NO: 1) | ACGTCCCTCTCGGACTTGG (SEQ ID NO: 2) |
| PTN | 6679543a1 | ATGTCGTCCCAGCAATATCAGC (SEQ ID NO: 3) | CCAAGATGAAAATCAATGCCAGG (SEQ ID NO: 4) |
| CXCL12 | 7305465a1 | TGCATCAGTGACGGTAAACCA (SEQ ID NO: 5) | TTCTTCAGCCGTGCAACAATC (SEQ ID NO: 6) |
| EFNB1 | 6753726a1 | TGTGGCTATGGTCGTGCTG (SEQ ID NO: 7) | CCAAGCCCTTCCCACTTAGG (SEQ ID NO: 8) |
| IGFBP4 | 6981086a1 | AGAAGCCCCTGCGTACATTG (SEQ ID NO: 9) | TGTCCCCACGATCTTCATCTT (SEQ ID NO: 10) |
| RBP1 | 6755300a1 | CTGAGCAATGAGAATTTCGAGGA (SEQ ID NO: 11) | GCGGTCGTCTATGCCTGTC (SEQ ID NO: 12) |
| VCAM1 | 31981430a1 | AGTTGGGGATTCGGTTGTTCT (SEQ ID NO: 13) | CCCCTCATTCCTTACCACCC (SEQ ID NO: 14) |
| Adamts5 | 6752976a1 | GGAGCGAGGCCATTTACAAC (SEQ ID NO: 15) | CGTAGACAAGGTAGCCCACTTT (SEQ ID NO: 16) |
| DCN | 6681143a1 | TCTTGGGCTGGACCATTTGAA (SEQ ID NO: 17) | CATCGGTAGGGGCACATAGA (SEQ ID NO: 18) |
| COL1A2 | 6680980a1 | GTAACTTCGTGCCTAGCAACA (SEQ ID NO: 19) | CCTTTGTCAGAATACTGAGCAGC (SEQ ID NO: 20) |

TABLE 2

Human PCR Primer Sets

| Gene | Forward | Reverse |
|---|---|---|
| Lmx1b | AACTGTACTGCAAACAAGACTACC (SEQ ID NO: 21) | TTCATGTCCCCATCTTCATCCTC (SEQ ID NO: 22) |
| AADC | GGGACCACAACATGCTGCTC (SEQ ID NO: 23) | CCACTCCATTCAGAAGGTGCC (SEQ ID NO: 24) |
| TH | TCATCACCTGGTCACCAAGTT (SEQ ID NO: 25) | GGTCGCCGTGCCTGTACT (SEQ ID NO: 26) |
| TrkB | AGGGCAACCCGCCCACGGAA (SEQ ID NO: 27) | TTGGTGGCCTCCAGCGGCAG (SEQ ID NO: 28) |
| En1 | CTGGGTGTACTGCACACGTTAT (SEQ ID NO: 29) | TACTCGCTCTCGTCTTTGTCCT (SEQ ID NO: 30) |
| Pitx3 | AGCTGCCTTTGCATAGCTCG (SEQ ID NO: 31) | AGCTGCCTTTGCATAGCTCG (SEQ ID NO: 32) |
| Smo | TATTCACTCCCGCACCAAC (SEQ ID NO: 33) | AGCCAGACATCCAGAACTC (SEQ ID NO: 34) |
| DAT | TTTCTCCTGTCCGTCATTGGC (SEQ ID NO: 35) | AGCCCACACCTTTCAGTATGG (SEQ ID NO: 36) |
| c-RET | CGACCTCATCTCATTTGCC (SEQ ID NO: 37) | AATCTTCATCTTCCGCCCC (SEQ ID NO: 38) |
| GFRA1 | AGGGAAATGATCTGCTGGAGGA (SEQ ID NO: 39) | CTCTGGCTGGCAGTTGGTAAAA (SEQ ID NO: 40) |
| GAPDH | ACCACAGTCCATGCCATCAC (SEQ ID NO: 41) | TCCACCACCCTGTTGCTGTA (SEQ ID NO: 42) |

Functional analysis of candidate molecules: Colonies of hESC in feeder-free conditions were removed from the tissue culture plates using a sterile cell scraper and partially dissociated by gentle pipetting. The cell clusters were resuspended in hESC culture medium without bFGF and transferred to ultra low-attachment plates (Corning Incorporated) for embryoid body (EB) formation. The medium was changed every day. After four days, the EBs were transferred to plates precoated with poly-L-ornithine (100 µg/ml, Sigma), and then laminin (20 µg/ml, Invitrogen) and cultured in hESC medium in the presence of heparin (100 µg/ml, Sigma) and the chosen molecule. The following final concentrations of the selected molecules were used: SDF-1 (100 ng/ml), PTN (100 ng/ml), IGF2 (100 ng/ml), IGFBP4 (500 ng/ml), and EFNB1 (200 ng/ml); all from R&D Systems (Minneapolis, Minn.). Half of the medium was replaced with fresh medium containing all molecules on days four and every 2-3 days after that. The cells were allowed to differentiate under these conditions for 10-14 days.

Protein Extraction and Western Blot Analysis:

Proteins extracted from BG01V2-derived cultures treated with SPIE, and cultures grown in the absence of SPIE, were used for Western blot analysis. Briefly, cells were washed in PBS and lysed in cold preparation of modified radioimmunoprecipitation buffer (Millipore) and treated with protease inhibitors, phenylmethylsulfonyl fluoride (1 mM), leupeptin (1 µg/ml), and aprotinin (2.5 KU). The lysates were sonicated for 10 s on ice and stored at $-80°$ C.

Twenty micrograms of protein was separated on a 4-12% Bis-Tris, or 3-8% Tris-acetate gel (Invitrogen) and transferred at $4°$ C. to a PVDF-FL membrane overnight. After transfer, the membrane was blocked in PBS containing 5% dried milk for one hr at room temperature. The membrane was washed three times with PBST for 15 mM and incubated with primary antibodies in PBST solutions containing 1% milk overnight at $4°$ C. The primary antibodies used were rabbit anti-MAP-2 (1: 2000; Millipore), rabbit anti-Nurr1 (1: 1000; Millipore). Mouse anti-actin antibody (1: 1000; Santa Cruz) was used as an internal loading control. The membrane was washed three times with PBST for 15 min, and then incubated for 1 hr at room temperature with IRDye 700 and IRDye 800 secondary antibodies (LI-COR Biosciences, Lincoln, Nebr.). After extensive washing, the blots were analyzed using the LI-COR Odyssey infrared imaging system (LI-COR Biosciences).

Electrophysiological Recordings:

The bathing solution was prepared to be similar in ionic composition and identical in osmolarity to the DMEM/F12 culture medium that the cells were grown in. It consisted of (mM): NaCl, 150; KCl, 4; $MgCl_2$, 1; $CaCl_2$, 1; $NaH_2PO_4$, 0.5; HEPES (hemi-sodium), 10; glucose, 18; sucrose, 24, pH 7.4, 348 mOsm. The pipette solution consisted of (mM): KCl, 140; $MgCl_2$, 2, EGTA, 11; $CaCl_2$, 1, HEPES, 10, pH 7.2. To this was added 4 mM of lucifer yellow CH (dipotassium). Stock solutions of GABA, acetylcholine, and glutamic acid were diluted 1:1000 on the day of use, and were applied by superfusion from a Y-tube (Murase et al., Neurosci. Lett. 103:56-63, 1989).

Cells were recorded by conventional whole cell recording using an Alembic VE-2 amplifier (Alembic Instruments, Montreal, Canada) operating at 100% series resistance compensation. Recordings were under the control of Pclamp v.7.0 (Molecular Devices, Sunnyvale, Calif.). In the search for h-currents, cells were held at $-60$ mV and stepped to $-100$ mV for one second, then back to $-60$ mV for one second. In the remaining voltage clamp recordings, the holding potential was $-70$ mV. Current-voltage curves were obtained by stepping the voltage from the holding potential to voltages of $-80$ to $+50$ mV in 10 mV increments. P/N leak subtraction (8 substeps) was used for all voltage step recordings. Current signals were filtered at 5 kHz and sampled at 25 kHz. Voltage signals were filtered at 2 kHz and sampled at 5 kHz.

Example 2

PA6 Cell Transformation

The original PA6 cell line, with DA-inducing properties, had a polygonal, flat morphology and showed contact inhibition (FIG. 1A). Transformation of the mouse stromal PA6-DA cells to the PA6-X cell phenotype in culture was marked by the appearance of morphologically altered cells. The morphology of cells changed from a polygonal to a more elongated fibroblast-like shape exhibiting long cytoplasmic extensions (FIGS. 1A, B). The transformed cell population grew to increasingly higher saturation densities, did not exhibit contact inhibition properties and often detached from tissue culture plates upon confluency. This transformation was an unpredictable event which was observed several times but was not directly related to the number of passages in culture. Once transformed to the PA6-X phenotype, reversion to the PA6-DA phenotype did not occur. Expression of the mesenchyme-associated markers such as alpha-smooth muscle actin (ASMA) and vimentin was also significantly down regulated in the transformed PA6 cells. The PA6-X1 cell subtype was derived from a separate culture, and had a phenotype intermediate between that of the PA6-DA and PA6-X cells and was contact inhibited.

MS5 cells, like PA6, are stromal cells and have been reported to carry properties of inductive signaling that promotes midbrain specific neural precursor differentiation (Barberi et al., Nature Biotechnol. 21:1200-1207, 2003; Perrier et al., Proc. Natl. Acad. Sci. USA 101:12543-12548, 2004). The MS5 cells used in this study were most likely a sub-type of the original MS5 cell line and did not support dopaminergic differentiation. The morphology and cellular behavior of MS5 cells and levels of ASMA and vimentin expression in these cells were generally similar to the PA6-X1 line.

Example 3

Assessment of Dopaminergic Inducing Effect of Feeder Cells

Figure 2A:
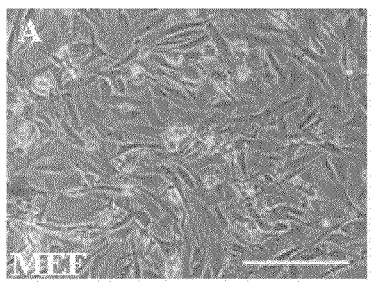
FIG. 2A through L is a series of digital images showing feeder-cell induced differentiation of hESC. Phase contrast images of confluent layers of (A) MEF cells; (B) mouse kidney cell line MM55K; (C) mouse stromal cell line MS5; (D) PA6-X1 cells; (E) PA6-X cells; (F) PA6-DA cells. Representative images of day 12 co-cultures of BG01V2 cells with (G) MEF cells; (H) MM55K cells; (I) MS5 cells; (J) PA6-X1 cells; (K) PA6-X cells; and (L) PA6-DA cells.
Figure 2B:
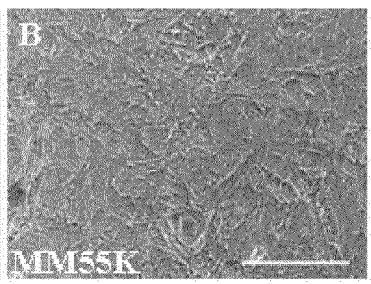
Figure 2C:
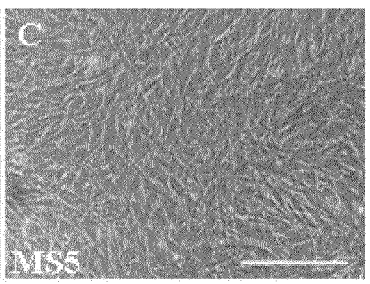
Figure 2D:
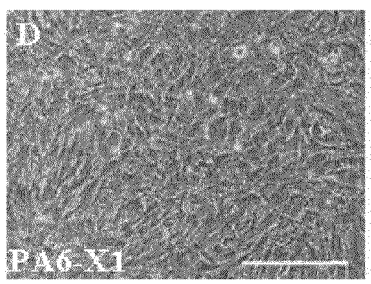
Figure 2E:
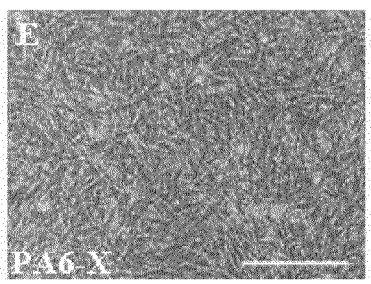
Figure 2F:
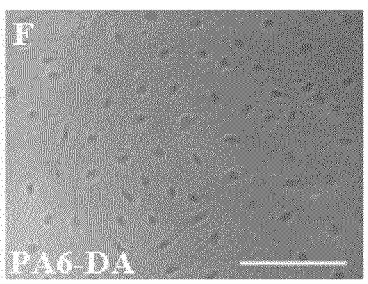
Figure 2G:
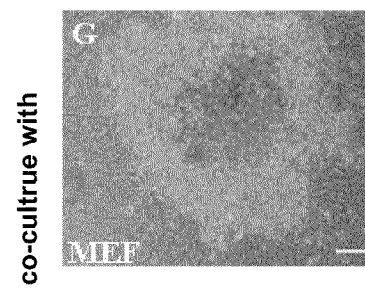
Figure 2H:
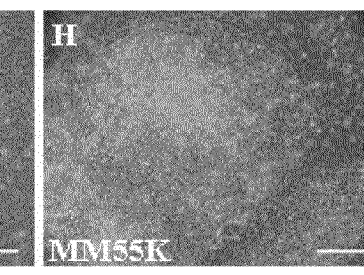
Figure 2I:
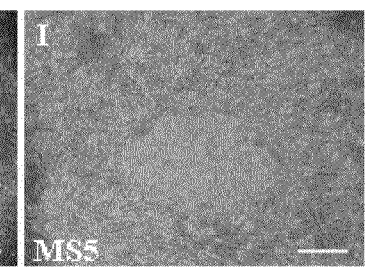
Figure 2J:
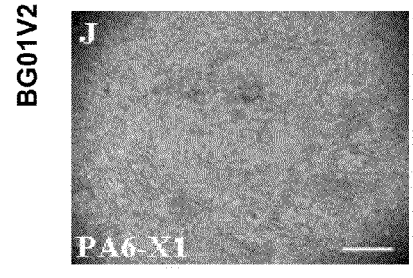
Figure 2K:
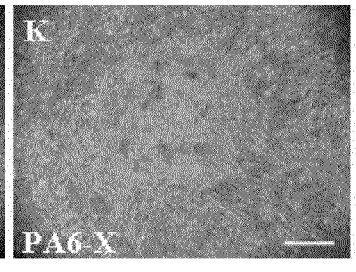
Figure 2L:

In order to test the ability of MEF, MM55K, MS5, PA6-X1, PA6-X and PA6-DA cell lines (FIG. 2A-F) in dopaminergic induction of hESC, small colonies of BG01V2 were co-cultured with each of the feeder cell lines for 12 days (FIG. 2G-L). The colonies grown on MEF, MM55K and PA6-DA showed increased survival and proliferation (FIGS. 2G, H, L). Colonies in co-culture with MEF seemed to undergo random differentiation, while cells in the center of colonies grew in multiple layers (FIG. 2G). Colonies cultured on MM55K appeared to grow as a monolayer with a tiled appearance similar to epithelial cells (FIG. 2H). MS5, PA6-X1 and PA6-X lines were less effective in growth and maintenance of hESC colonies (FIG. 2 I-K). After 7 days colonies ceased to grow in size and at day 12 of co-culture, significantly fewer numbers of hESC were observed in these cultures. The PA6-DA cell line was superior to all other lines in promoting survival and inducing ectodermal differentiation, as indicated by the presence of rosette-like arrangements and cells with clear neuronal morphology.

Undifferentiated stem cells were monitored by expression of Oct3/4 in all co-culture systems after 12 days. Percentages of Oct3/4+ colonies grown on MEF feeders and MM55K cells were 58±18% and 82±8%, respectively, as compared to 82±10% colonies expressing Oct3/4+ in co-culture with the PA6-DA cells. Also, percentages of Oct3/4+ cells within colonies maintained on PA6-DA cells were significantly higher, as compared to all other feeder lines.

Figure 3:
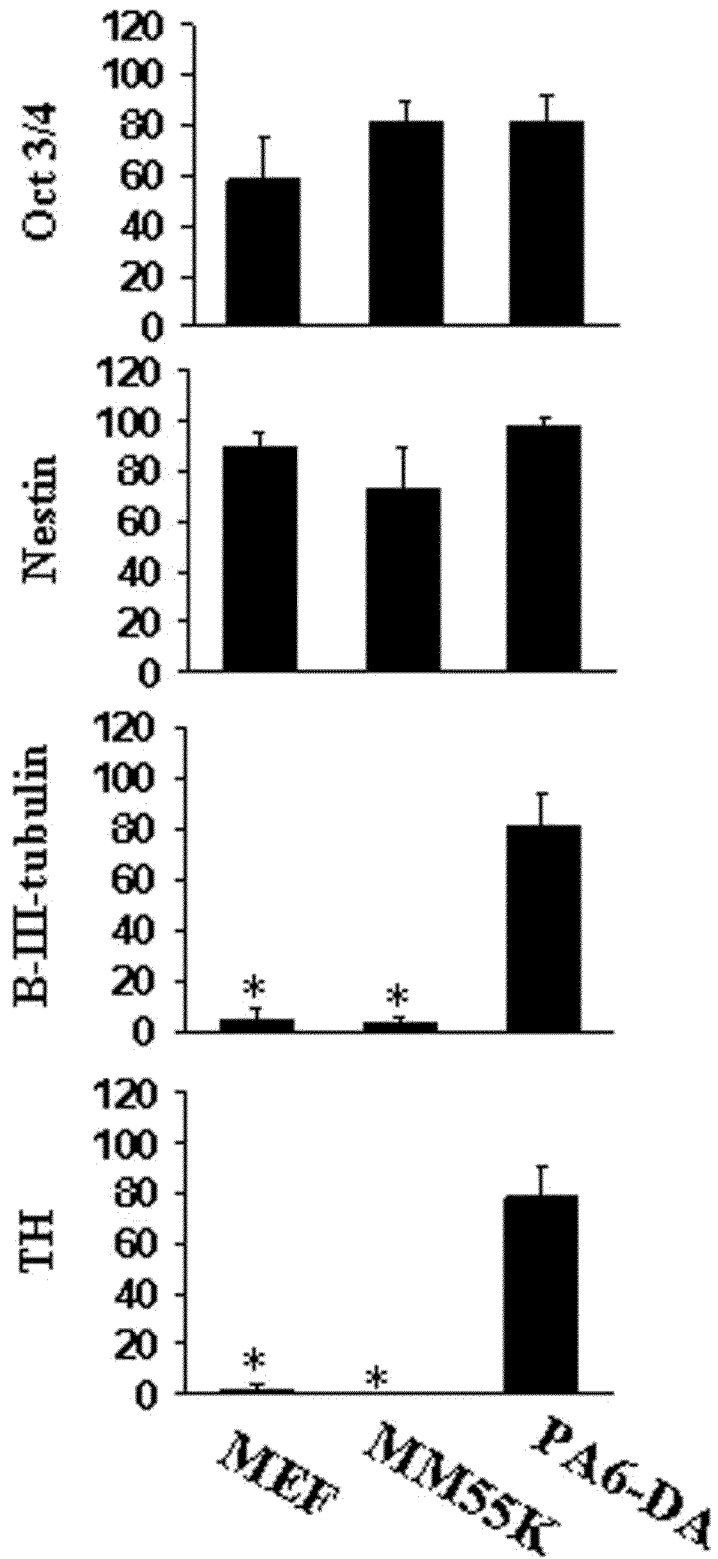
FIG. 3 is a bar graph showing percentage of colonies expressing Oct3/4, Nestin, β-III tubulin, and TH after 12 days of co-culture with MEF, MM55K, or PA6-DA feeder cells. Error bars indicate SD. Data represent 60 colonies from three independent experiments. * P<0.0001 compared to PA6-DA co-cultures.

The majority of colonies grown on MEF, MM55K or PA6-DA cells contained cells expressing the immature neuroepithelial cell marker, nestin. Less than 1% of colonies cultured on MEF and MM55K contained cells immunoreactive to the dopaminergic neuronal marker TH. In contrast, 78±13% of colonies cultured on PA6-DA cells contained large numbers of TH+ neurons. Neurons expressing β-III-tubulinwere detected in 5±5% and 3±3% of colonies grown on MEF and MM55K respectively, whereas co-culture with PA6-DA cells resulted in 82±13% β-III-tubulin+colonies. The average percentages of Oct3/4, nestin, β-III-tubulin and TH expressing colonies cultured on MEF, MM55K and PA6-DA cells are presented as bar graphs in FIG. 3. The cell lines PA6-X1, PA6-X, and MS5 were unable to support the survival of hESC for 12 days. Therefore, differentiation of hESC in co-culture with these three cell lines could not be assessed.

Example 4

Analysis of Gene Expression

By comparing gene expression of the PA6-DA cell line to the five cell lines lacking SDIA activity, PA6-X1, PA6-X, MS5, MEF and MM55K, a set of candidate genes were identified as potential dopaminergic inducing elements. In total, 288 genes were preferentially expressed (Z ratio≥3.0) in PA6-DA cells as compared to the PA6-X cell subtype. The majority of these genes were also significantly up-regulated in PA6-DA cells as compared to the transformed stromal cell lines, PA6-X1, PA6-X, MS5, and the MM55K and MEF cells. Biological processes were available for 159 genes of the 288 genes analyzed using the FatiGO web tool. The functions of these genes included 50 different categories at the most basic level. Genes corresponding to cellular metabolic process and regulation of biological process were the most highly represented categories containing 52% and 43% of the genes respectively. Approximately 23% and 19% of genes were categorized in anatomical structure development and cellular developmental process.

In order to classify genes predominantly involved in biological processes and pathways related to CNS development among the 288 up-regulated genes, we used more advanced gene ontology at specificity level six. Table 3 illustrates gene clusters associated with the gene ontology of various biological process related to brain development at FatiGO specificity level six, as well as the gene's distribution in categories at level three.

TABLE 3

Gene clusters highly expressed in PA6-DA cells.

| GO Biological Process at Level 6 | Gene | UniGene Accession No. | % of Genes | Z ratios* PA6-X | MM55K |
|---|---|---|---|---|---|
| Neurogenesis | IDB4 | NM_031166.1 | 5.88 | 3.16 | 2.57 |
| | EFNB1 | NM_010110.2 | | 8.56 | 7.43 |
| | CXCL12 | NM_013655.2 | | 16.27 | 14.34 |
| | TIMP2 | NM_011594.2 | | 3.32 | 1.66 |
| | MYH10 | NM_175260.1 | | 9.62 | 5.18 |
| | THY1 | NM_009382.2 | | 3.15 | 2.90 |
| | RUNX1 | NM_009821.1 | | 4.28 | 4.71 |
| | NOTCH1 | NM_008714.2 | | 3.02 | 3.99 |
| CNS development | OTX1 | NM_011023.2 | 3.68 | 3.22 | 2.04 |
| | IDB4 | NM_031166.1 | | 3.16 | 2.57 |
| | CXCL12 | NM_013655.2 | | 16.27 | 14.34 |
| | MYH10 | NM_175260.1 | | 3.15 | 2.90 |
| | NOTCH1 | NM_008714.2 | | 3.02 | 3.99 |
| Tissue development | MGLAP | NM_008597.2 | 3.68 | 9.42 | 1.40 |
| | PTN | NM_008973.1 | | 13.50 | 14.60 |
| | SOX9 | NM_011448 | | 11.62 | 6.33 |
| | OTOR | NM_020595 | | 4.04 | 4.61 |
| | NOTCH1 | NM_008714.2 | | 3.02 | 3.99 |
| Wnt receptor signaling pathway | SFRP1 | NM_013834.1 | 2.94 | 14.24 | 14.53 |
| | SFRP2 | NM_009144.1 | | 3.16 | 3.09 |
| | FRZB | NM_011356.2 | | 3.44 | 2.56 |
| | PPAP2B | NM_080555.1 | | 3.37 | 7.36 |
| Cellular morphogenesis during differentiation | EFNB1 | NM_010110.2 | 2.94 | 8.56 | 7.43 |
| | CXCL12 | NM_013655.2 | | 16.23 | 14.34 |
| | THY1 | NM_009382.2 | | 9.62 | 5.18 |
| | NOTCH1 | NM_008714.2 | | 3.02 | 3.99 |
| Neural crest cell differentiation | EFNB1 | NM_010110.2 | 2.21 | 8.56 | 7.43 |
| | SEMA3F | NM_011349.2 | | 4.66 | 0.40 |
| | SOX9 | NM_011448 | | 11.62 | 6.33 |
| Regulation of cell migration | CXCL12 | NM_013655.2 | 2.21 | 16.23 | 14.34 |
| | THY1 | NM_009382.2 | | 9.62 | 5.18 |
| Cell fate specification | SOX9 | NM_011448 | 2.21 | 11.62 | 6.33 |
| | NOTCH1 | NM_008714.2 | | 3.02 | 3.99 |
| Neural tube development | LTAP | NM_033509.2 | 0.74 | 3.21 | 2.18 |

*Expression levels of genes in PA6-DA as compared to PA6-X and MM55K cells are presented as Z ratios.

Focusing on soluble secretory molecules and gene products with a possible role in CNS development and regulation of neurogenesis, stromal cell-derived factor 1 (SDF-1/CXCL12), pleiotrophin (PTN), insulin-like growth factor 2 (IGF2), insulin-like growth factor binding protein 4 (IGFBP4), and ephrin B1 (EFNB1) were identified as factors potentially responsible for the dopaminergic inducing activity. These genes were among the most up-regulated in PA6-DA as compared to PA6-X or MM55K cells, each having a seven-fold greater Z-ratio. Relative expression of these genes in PA6-DA versus each cell type is presented in Table 4.

TABLE 4

Relative expression of the five candidate genes in the PA6-DA cell line

| | | Z-ratios | | | | |
|---|---|---|---|---|---|---|
| Genes | UniGene Accession | PA6-DA/ PA6-X | PA6-DA/ PA6-X1 | PA6-DA/ MS5 | PA6-DA/ MM55K | PA6-DA/ MEF |
| CXCL12 | NM_013655.2 | 16.27 | 16.92 | 15.08 | 14.34 | 9.96 |
| EFNB1 | NM_010110.2 | 8.56 | 9.26 | 8.40 | 7.43 | 7.01 |
| PTN | NM_008973.1 | 13.50 | 14.58 | 12.17 | 14.60 | 5.70 |
| IGF-II | NM_010514.1 | 13.19 | 13.83 | 11.63 | 13.52 | 3.28 |
| IGFBP4 | NM_010517.2 | 14.18 | 13.39 | 12.70 | 12.50 | 5.73 |

Figure 4:
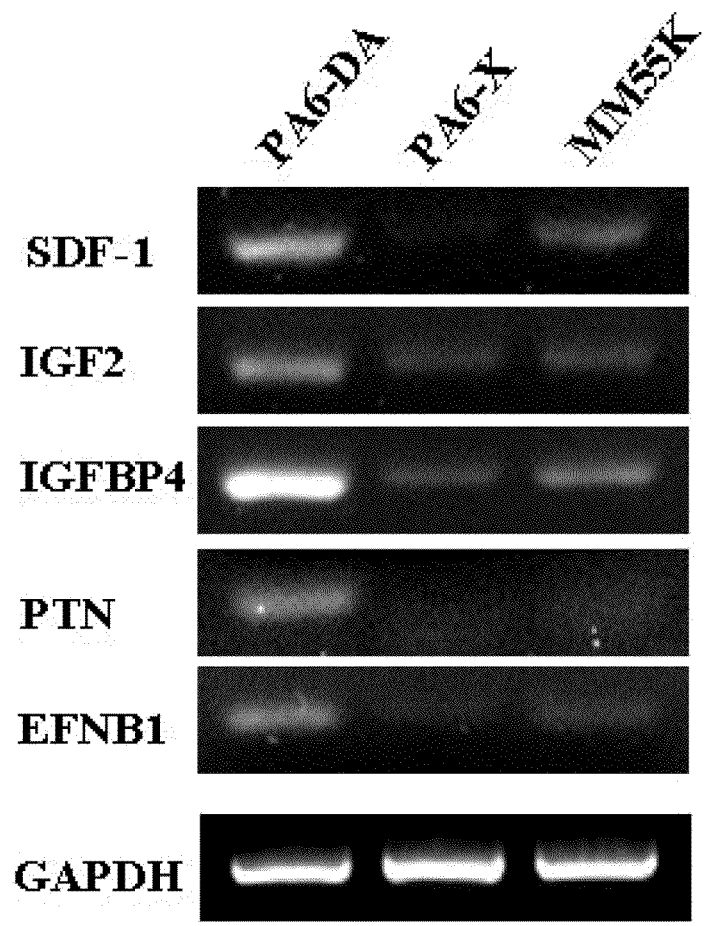
FIG. 4 is a series of digital images of RT-PCR results in PA6-DA, PA6-X, and MM55K cell lines for five candidate genes selected by microarray analysis. GAPDH was amplified as an internal control under the same conditions.

Differences in these transcripts as determined by RT-PCR, were in strong correlation with the microarray results (FIG. 4). As shown in Table 3, the selected genes SDF-1(CXCL12) and EFNB1 were included in the CNS and neuronal development category, while PTN was placed in the tissue development gene cluster by FatiGO. IGF2 and IGFBP4 were not included in categories related to neural development, but were assigned to organ morphogenesis and cell growth. In addition, PTN, fibroblast growth factor-10 (FGF10), and serpin peptidase inhibitor, clade E (SERPINE2) also known as glial-derived neurite promoting factor, were classified as heparin binding factors by gene ontology in molecular function at level six. SERPINE2 and FGF10 were highly expressed in PA6-DA cells by approximately three- and 14-fold respectively, as compared to both PA6-X and MM55K cells.

Figure 5:
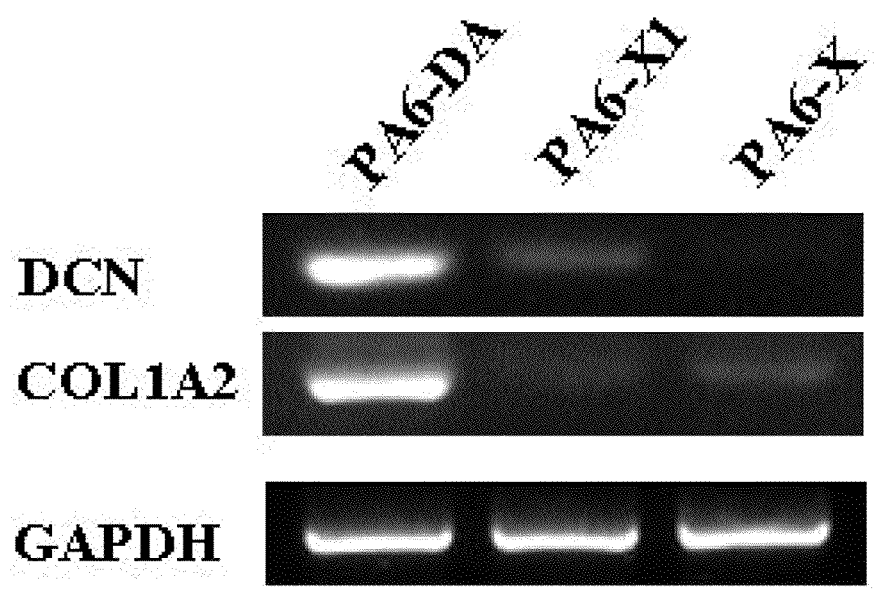
FIG. 5 is a series of digital images of RT-PCR results in PA6-DA, PA6-X, and MM55K cell lines for decorin and procollagen type I. GAPDH was amplified as an internal control under the same conditions.

As illustrated in FIG. 1, the cytoskeletal organization of the transformed PA6 cells was drastically different from that of the potent PA6-DA cells. Results from the gene expression analysis also revealed that several collagens, particularly collagen type I, and decorin were down-regulated in the PA6-X1 and PA6-X as compared to PA6-DA cells. This alteration may have arisen from inhibition of synthesis of proteoglycans such as decorin, and of fibril forming collagens modifying extracellular matrix deposition. The alteration of collagen and decorin expression in all PA6-derived cell lines was validated by RT-PCR (FIG. 5). The PA6-X1 line did not promote dopaminergic differentiation, but supported cell survival of hESC in the co-culture system for a longer time period as compared to the completely transformed PA6-X cells.

A number of other factors were up-regulated, but to a significantly lesser degree. These included members of the TGF-β family and factors involved in the Wnt signaling pathway. It has been suggested that these factors play a critical role in controlling neuronal fate and the establishment of the dopaminergic phenotype (Farkas et al., *J. Neurosci.* 23:5178-5186, 2003; Castelo-Branco and Arenas, *Neurodegener. Dis.* 3:5-11. 2006). Significantly higher levels of the soluble Wnt inhibitor secreted Frizzled-related protein 1(sFRP-1) were also detected in PA6-DA cells, which is suggested to have an inhibitory effect on ventral midbrain neuronal development (Z ratio≥14) than sFRP-2, which promotes dopaminergic neurogenesis and maturation (Z ratio>3).

Example 5

Procedures for Assessing SDIA

To further validate that the selected molecules are directly responsible for the SDIA effect of PA6 cells, various protocols for exposing hESC to SDF-1 (100 ng/ml), PTN (100 ng/ml), IGF2 (100 ng/ml), IGFBP4 (500 ng/ml), and EFNB1 (200 ng/ml) were tested.

Initially, a previously established protocol was used to test the effects of PA6 conditioned medium (Vazin et al., *Stem Cells* 26:1517-1525, 2008). In this culture system containing hESC differentiation medium, the majority of isolated hESC did not attach to the uncoated surfaces and did not survive well or form colonies.

In order to promote cell adherence, the plates were coated with various extracellular matrix substrates, such as fibronectin, poly-L ornithine/laminin or laminin A few colonies attached to the fibronectin and poly-L ornithine/laminin, but cell survival, proliferation, and differentiation was limited under these conditions. The loss of viability may have been a response to the rapid change in their environment.

To enhance cell survival, hESC maintained in feeder-free conditions (FIGS. 6A, B) were isolated and cultured in low-attachment plates to form embryoid bodies (EBs) in hESC medium lacking the mitogen bFGF (FIG. 6C). Prior to formation of EBs, immunocytochemical analysis of expression of the stem cell markers Oct3/4 and SSEA-4 was carried out to verify that the hESC were in an undifferentiated state (FIGS. 6E, F). After four days, resultant EBs (FIG. 6D) were transferred to poly-L ornithine/laminin coated dishes and were allowed to differentiate in the presence of heparin and selected molecules.

Example 6

In Vitro Functional Analysis of Candidate Molecules

Figure 7A:
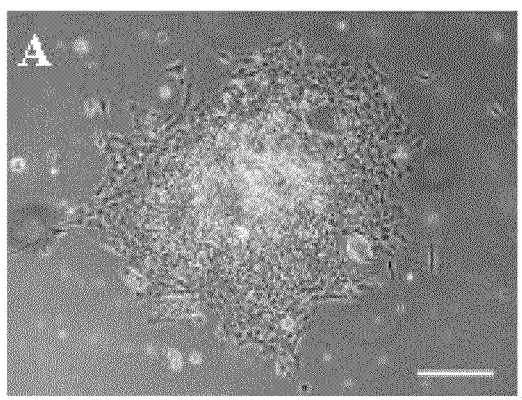
FIG. 7A through D is a series of digital images showing EBs transferred to poly-L-ornithine/laminin coated dishes and treated with SDF-1, IGF2, IGFBP4, PTN, EFNB1, and heparin. After three days of culture, the EBs attached to the plates and differentiated into neuroectodermal cells in rosette-like structures and cells with a clear neuronal morphology (A, B). In contrast EBs cultured in medium containing heparin in the absence of the other molecules did not adhere and attached colonies exhibited poor cell survival (C, D). Scale bars=200 µm.
Figure 7B:
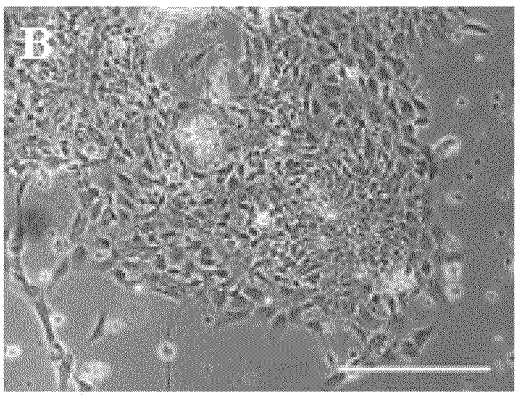
Figure 7C:
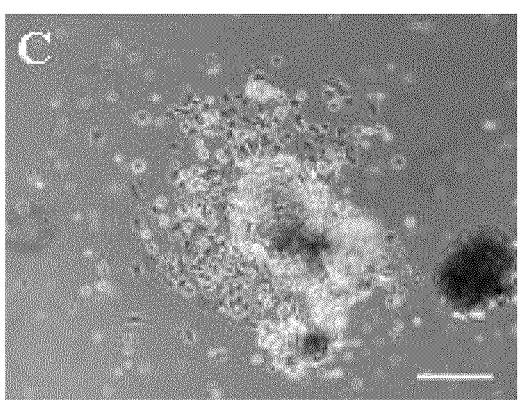
Figure 7D:
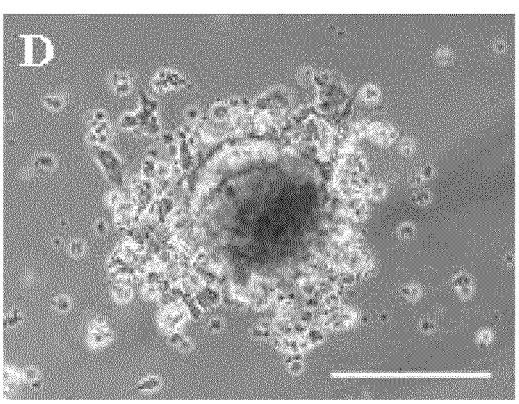

The majority of EBs exposed to the selected factors in hESC culture medium attached to the poly-L ornithine/laminin substrate, formed radial glia scaffolds (FIG. 7A), and developed into neural rosettes and neurons after three days in culture (FIG. 7B). In contrast, less than 10% of EBs cultured in the hESC medium alone, in the presence of heparin, attached to the culture dishes. In addition, under the latter condition there was a substantial decrease in cell viability (FIGS. 7C, D). To determine whether the neural rosettes induced by these factors contained mesencephalic-restricted neural progenitor cells, analysis of Msx1 and TH expression was carried out after 10 days. The majority of colonies contained numerous TH+ neurons, predominantly found in the periphery of colonies. Cells in the central, denser areas of colonies were relatively undifferentiated at this time, as illustrated by expression of the midbrain progenitor marker Msx1. TH was detected in the majority of β-III-tubulin-expressing neuronal cells.

To further characterize and separate the role of the candidate molecules in TH+ cell induction, EB cultures were exposed to various combinations of inducing factors followed by immunocytochemical marker analysis after 10 days of differentiation. The results indicated that IGF2 enhanced survival of the proliferating NPC. In contrast, IGFBP4 reduced the survival of the differentiating hESC, possibly by inhibiting IGF2.

Figure 8:
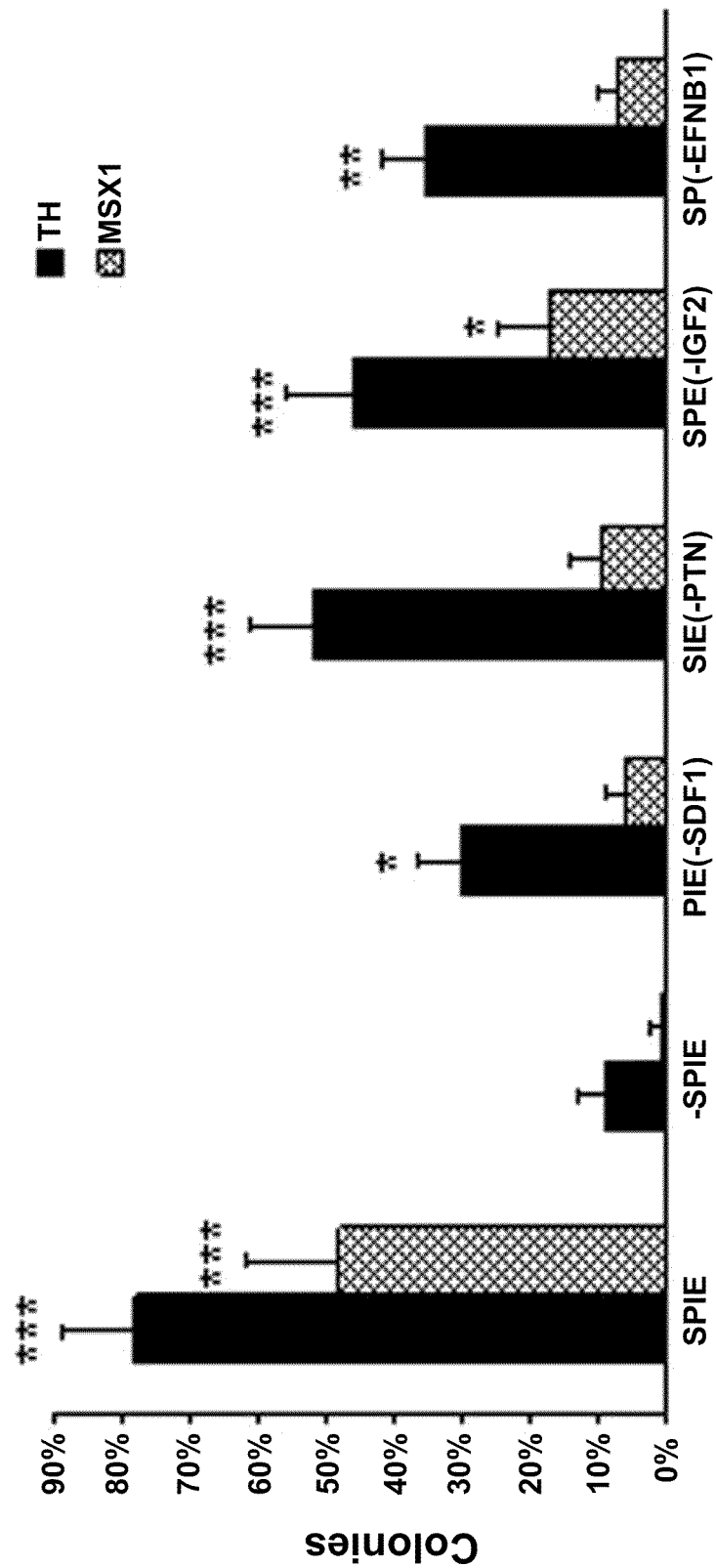
FIG. 8 is a bar graph showing percentage of colonies expressing TH and Msx1 after 10 days exposure to combinations of the four factors SDF-1 (S), PTN (P), IGF2 (I), and EFNB1 (E) (SPIE). P<0.05,  P<0.01, * P<0.001 as compared to the untreated condition (-SPIE) (Tukey-Kramer multiple comparisons following one way analysis of variance).

The combination of SDF-1, PTN, IGF2, and EFNB1 was more efficient than the combination of five factors including IGFBP4. The combination of the four factors SDF-1, PTN, IGF2, and EFNB1 was therefore termed "SPIE." The absence of any one component of SPIE resulted in a decrease in DA induction and differentiation, as compared to cultures exposed to complete SPIE (FIG. 8). Omission of SDF-1 or EFNB1 decreased the number of TH+ colonies by more than 50%. Cultures lacking PTN or IGF2 contained approximately 33% and 41% less TH expressing colonies respectively. Exclusion of SDF-1 or EFNB1 also had the largest effect on generation of midbrain NPC as indicated by 86% and 85% decrease in Msx1+ colonies, respectively, as compared to treatment with all four factors (FIG. 8). Exclusion of PTN or IGF2 decreased the percentage of colonies containing Msx1-expressing cells from 48%, to 17% and 10%, respectively. In addition, numbers of TH+ cells within colonies were greatly decreased in conditions lacking any one of the factors, although the number of TH+ cells within colonies could not be quantified.

Figure 9A:
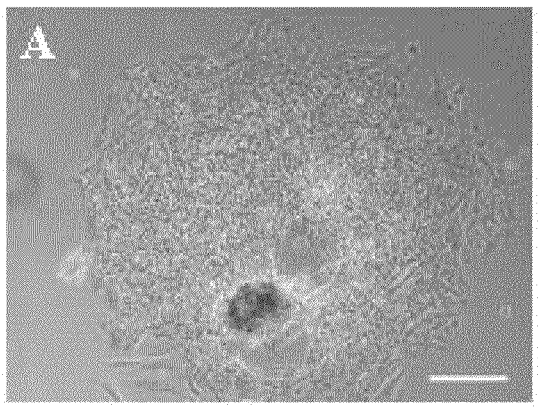
FIG. 9A through D is a series of digital images showing BG02-derived EBs differentiated in the present of SDF-1, IGF2, IGFBP4, PTN, EFNB1 (A) or in the absence of any factors (B) three days after seeding on adherent cultures and BG03-derved EBs in the presence of the five candidate factors (C) or in cultures that did not contain the molecules (D). Scale bar=200 µm.
Figure 9B:
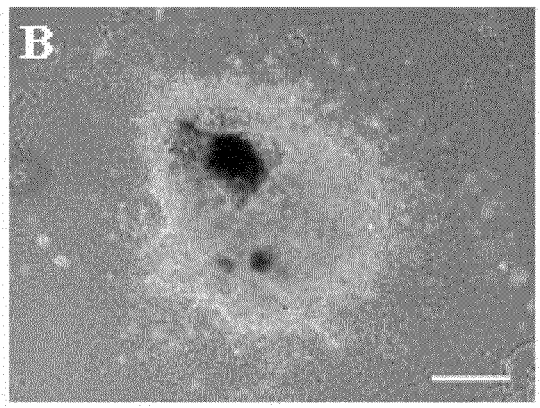

To determine whether the synergistic action of the candidate molecules represents a general mechanism for the induction of DA neurons from hESC, two other hESC lines, BG02 and BG03, with normal karyotypes were analyzed. EBs derived from the BG02 line showed an overall poor survival, and only a few colonies attached and remained in culture after three days. These cultures could not be maintained for longer than 5 days. Colonies of differentiating BG02 cells in the presence of selected factors showed somewhat enhanced survival, and cells with a neuronal morphology were found within these colonies three days after the EBs were transferred to adherent cultures (FIG. 9A). Conversely, cells within colonies that were grown in the absence of the molecules primarily had an epithelial morphology and did not contain cells with recognizable neuronal appearance (FIG. 9B). After 5 days of differentiation, TH+ neurons were found in treated cultures, but were completely absent in the untreated condition. Of note, the expression of Msx1 was found neither in treated nor in control conditions.

Figure 9C:
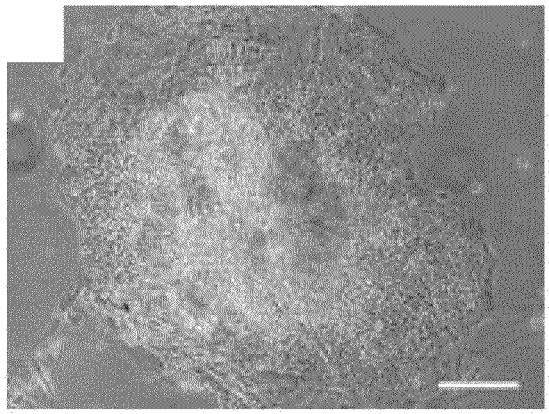
Figure 9D:
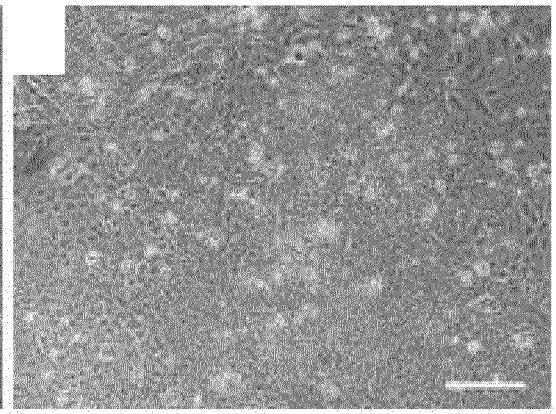

In contrast to BG02 cells, EBs derived from the BG03 cell line survived well either in the presence or absence of SPIE. The BG03-derived EBs that were exposed to the differentiation factor combination differentiated into rosettes (FIG. 9C), morphologically similar to those seen in SDIA-induced cultures. In contrast, colonies in the untreated cultures had a more uniform appearance and the emergence of rosettes in theses cultures was less than the cultures stimulated by the five molecules (FIG. 9D). When these EBs were allowed to differentiate for 10 days, more that 90% of colonies were Msx1+ with extensive networks of TH+ neuronal cells. Also, the majority of cells within each colony were Msx1+.

Example 7

Molecular and Electrophysiological Characterization of Differentiated Cells

Figure 10A:
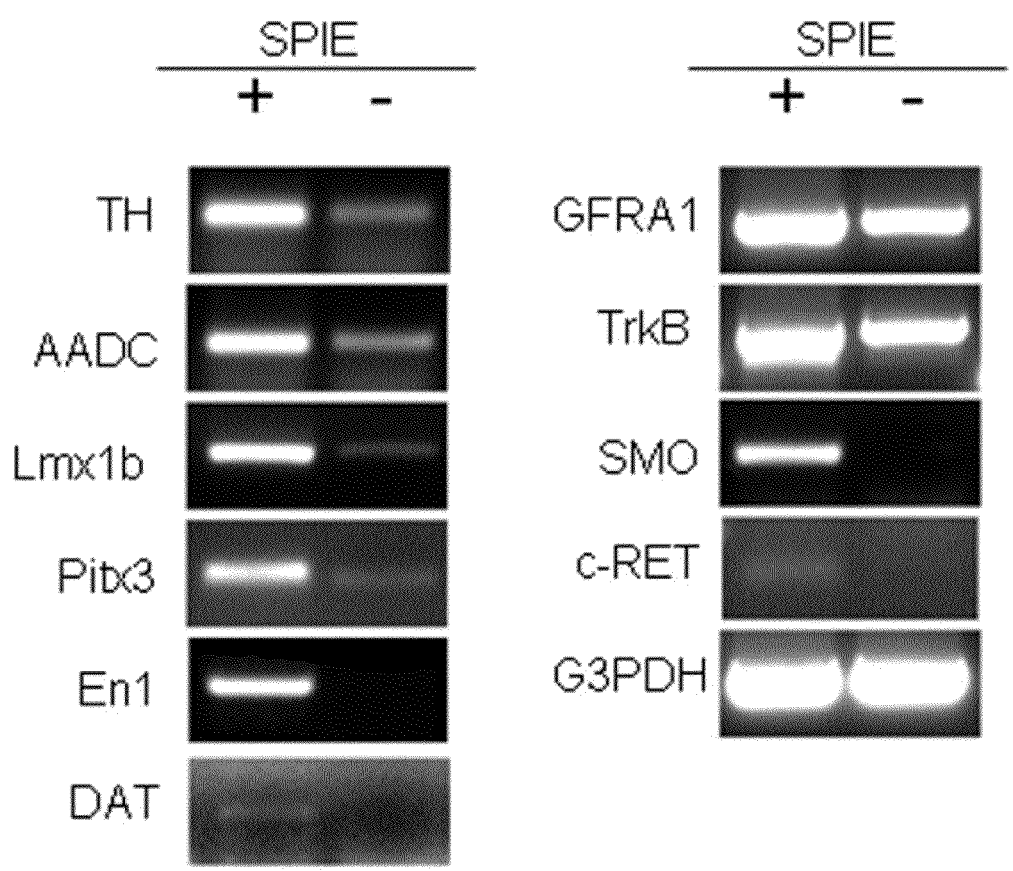
FIG. 10A is a series of digital images of agarose gels stained with ethidium bromide showing RT-PCR showing the effect of SPIE treatment on differentiation of BG01V2 cells to midbrain-specific DA neurons after 17 days. TH, tyrosine hydroxylase; AADC, aromatic L-amino acid decarboxylase; Lmx1b, LIM homeobox transcription factor 1b; Pitx3, paired-like homeobox transcription factor 3; En1, engrailed 1; DAT, dopamine transporter; GFRA1, GDNF family receptor alpha 1; TrkB, neurotrophic tyrosine kinase receptor type 2; SMO, smoothened; c-RET, ret proto-oncogene; G3PDH, glyceraldehydes-3-phosphate dehydrogenase (internal control).

RT-PCR and Immunoblot Analysis of SPIE-Treated Cultures:

Expression of markers involved in midbrain DA neuron development was assessed by RT-PCR in SPIE-treated and untreated cultures after 17 days of culture (FIG. 10A). LIM homeobox transcription factor 1b (Lmx1b), and the enzymes of the dopamine synthetic pathway, TH and aromatic L-amino acid decarboxylase (AADC), were detected at substantially higher levels in cultures influenced by SPIE, as compared to randomly-differentiated cultures. Midbrain specific paired-like homeodomain transcription factor 3 (Pitx3) and engrailed 1 (Ent) were expressed in SPIE-treated cultures, but not detected in untreated cultures. Expression of receptors GFR1 and c-RET for glial cell line-derived neurotrophic factor, was upregulated by SPIE. Increased expression of the brain-derived neurotrophic factor receptor, TrkB, and the smoothened (SMO) receptor was also confirmed in SPIE treated cultures. Neurons generated in the presence of SPIE also expressed the dopamine transporter (DAT) which is exclusively found in midbrain DA neurons.

Figure 10B:
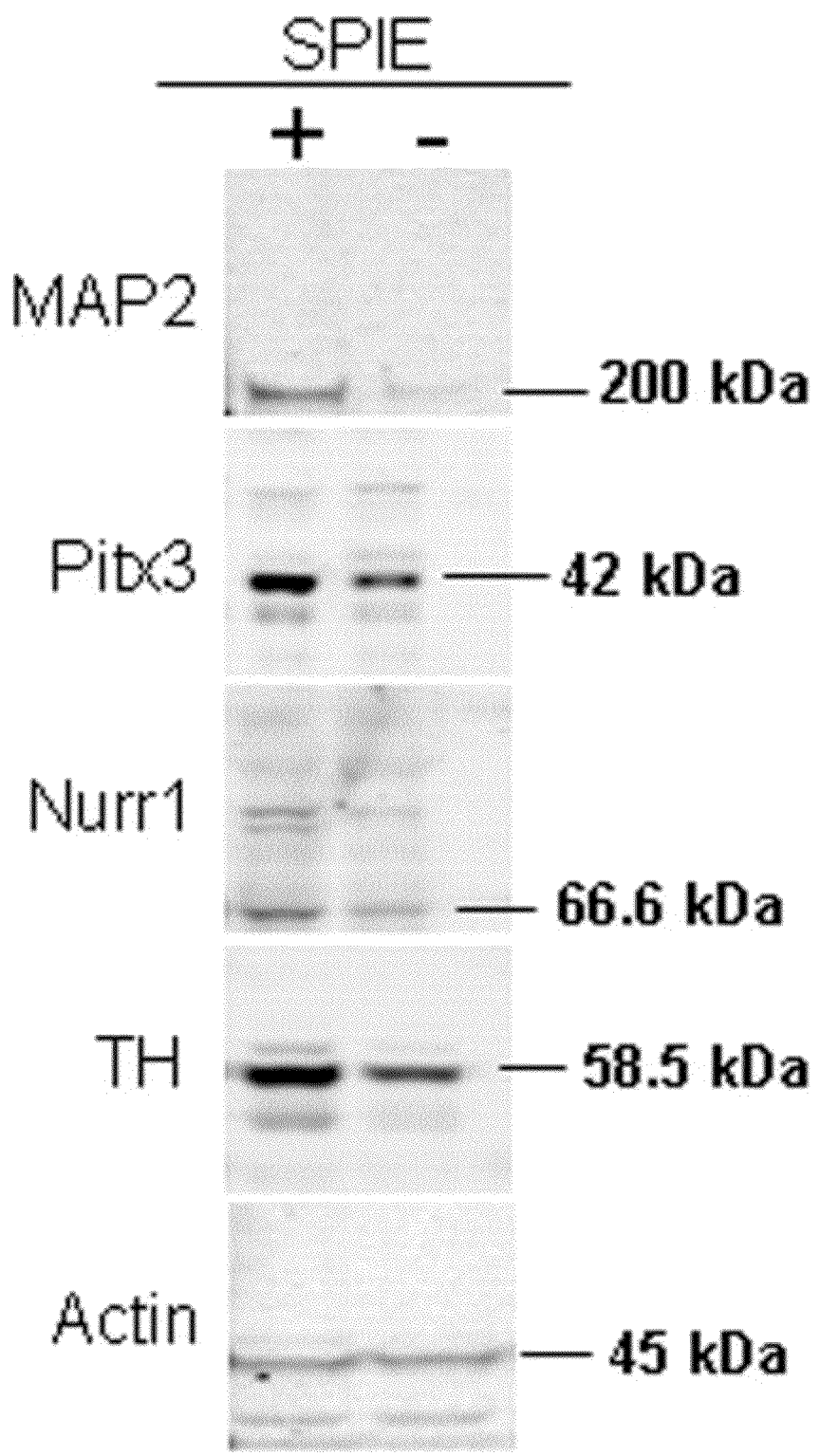
FIG. 10B is a series of digital images of Western blots showing increased levels of MAP-2, Pitx3, Nurr1, and TH proteins in cells treated with SPIE as compared to untreated cultures. The housekeeping gene actin was used as an internal loading control.

Western blot analysis confirmed expression of the MAP-2, Nuclear receptor 1 (Nurr1), and TH proteins (FIG. 10B). In agreement with previously obtained immunostaining data, TH and MAP-2 levels were increased by SPIE treatment. Nurr1 was also detected in untreated cultures, but was increased by SPIE. The Pitx3 antibody detected a band at the expected molecular weight (42 kDa), which was increased in the SPIE-treated cultures (FIG. 10B). In addition, the Pitx3 antibody detected non-specific or unknown bands at approximately 95 and 145 kDa, and these bands were not increased by SPIE.

Figure 11A:
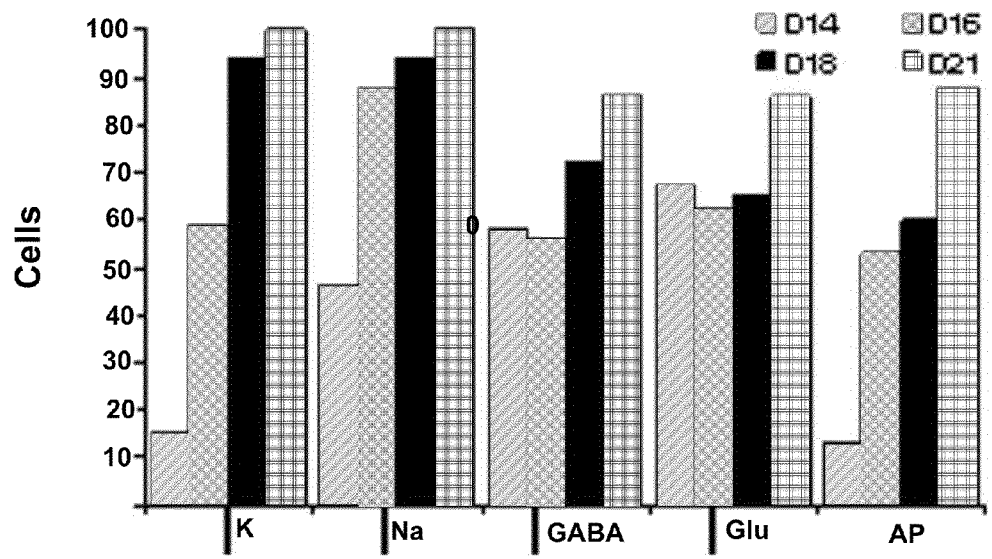
FIG. 11A through G is a series of graphs showing electrophysiological analysis of BG01V2-derived cultures differentiated by SPIE. (A) Bar graph showing percentage of cells eliciting sodium ($I_{Na}$), potassium ($I_{K}$), GABA-evoked ($I_{GABA}$), and glutamate-evoked a ($I_{Glu}$) currents and percentage of cells capable of generating action potentials (AP) after 14, 16, 18, and 21 days. Representation of cumulative log-normal distribution of maximal potassium currents (B), sodium currents (C), and GABA currents (D) over time. ●, 14 days; ■, 16 days; ▼, 18 days; ▲, 21 days SPIE. (E) Hoffman modulation contrast image of a cell showing electrical excitability (top left) as shown by strong inward sodium current (top right) and outward potassium current (bottom right) under voltage clamp at day 21 of differentiation and a strong AP obtained by a 90 pA current step from a member potential of –112 mV with an after hyperpolarization (bottom left). (F) An example of a neuron capable of generating multiple APs after 18 days of differentiation. (G) Spontaneous, miniature postsynaptic currents recorded from a cell at day 21 of differentiation.

Electrophysiological Studies:

After 21 days of differentiation, about 80% of colonies contained numerous TH+ neurons. Cell counting revealed that 45±12% of the total number of cells were neurons, as determined by expression of the mature neuronal marker MAP-2. Double staining showed co-localization of TH in 71±8% of MAP-2+ neurons. TH+ cells which showed a fusiform shape typical of DA neurons (Berger et al., Neuroscience 7:193-205, 1982) were selected for electrophysiological recordings after 14, 16, 18, and 21 days of differentiation. The fraction of excitable cells, as measured by voltage gated sodium and potassium currents, and the fraction of cells showing sensitivity to the neurotransmitters GABA, and glutamate showed progressive changes (FIG. 11A).

Figure 11B:
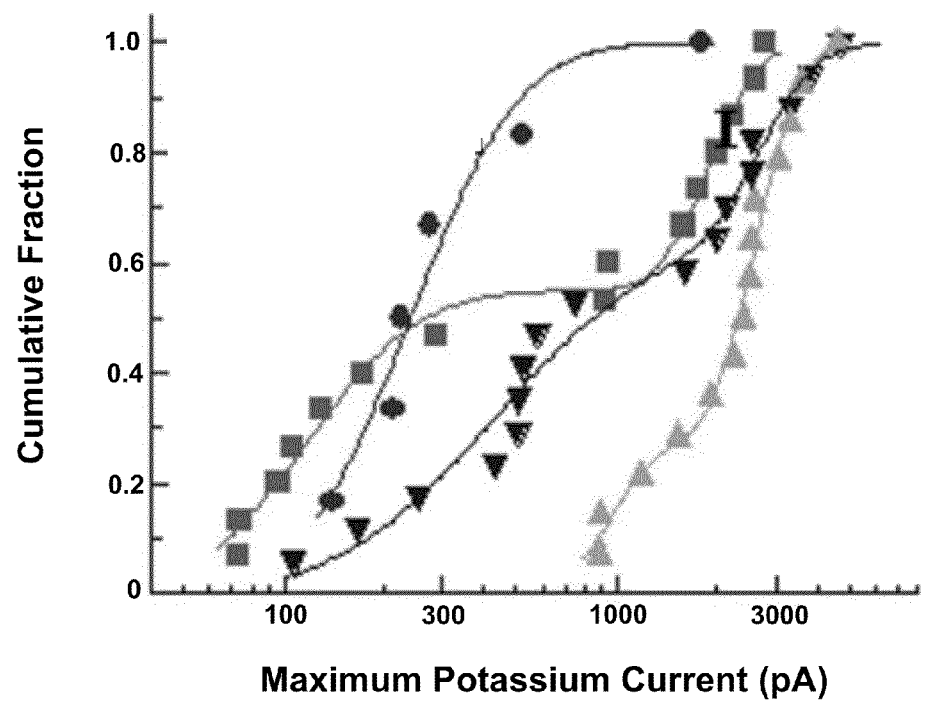
Figure 11C:
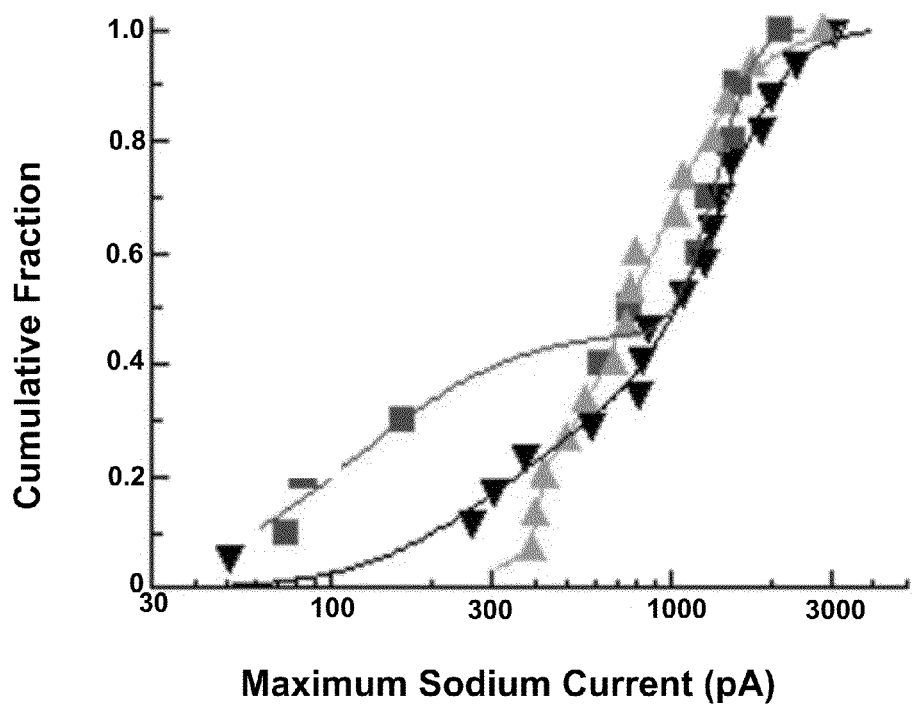
Figure 11D:
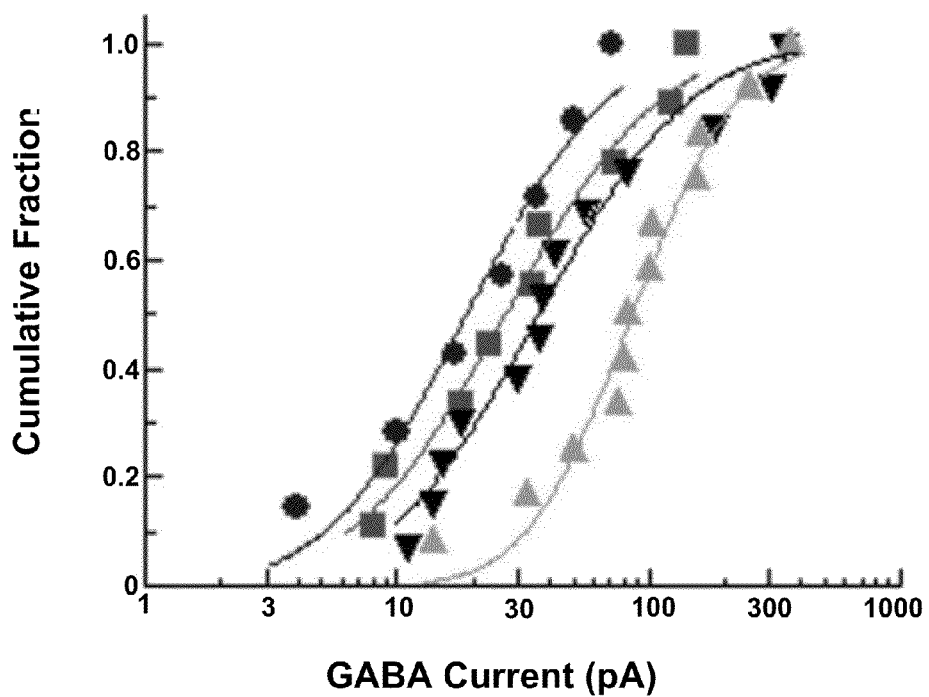
Figure 11E:
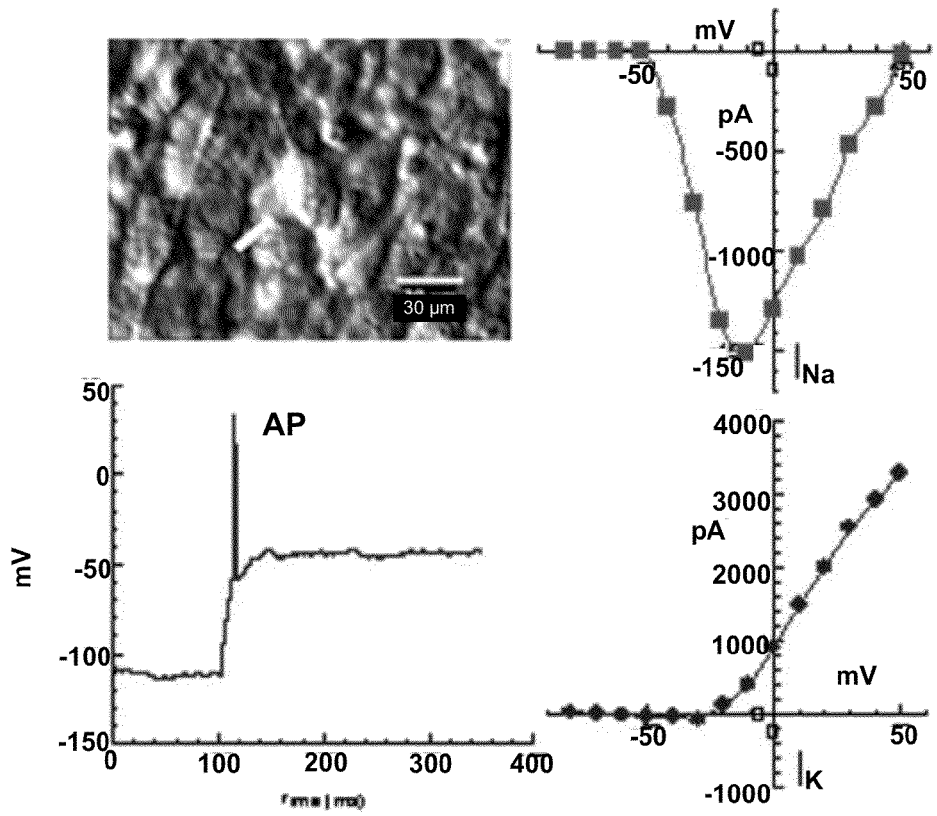
Figure 11F:
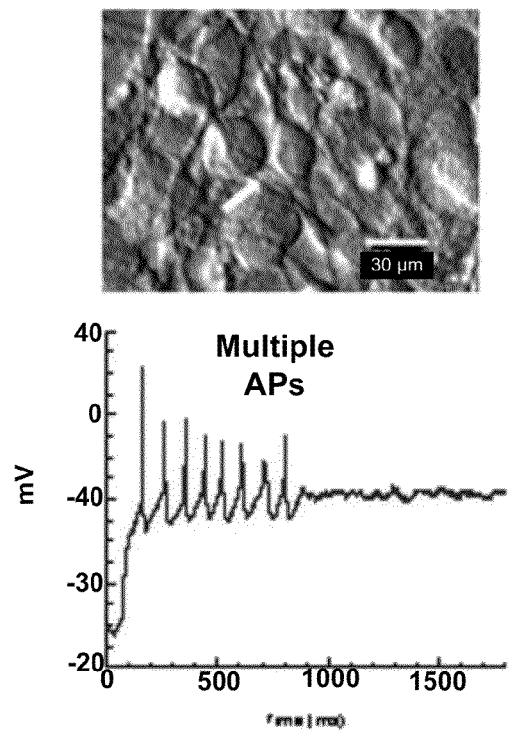
Figure 11G:
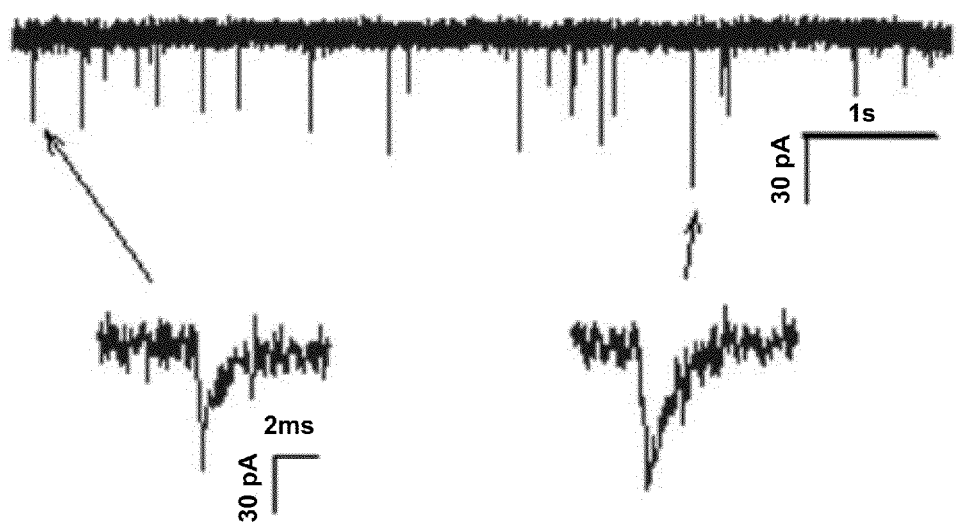

The maximum current values for potassium (FIG. 11B) and sodium (FIG. 11C) generally had a bimodal (log-normal) distribution. For both currents, the fraction of the smaller mode shrank with time while the amplitude of the larger mode remained fairly constant. The GABA-induced currents also showed progressive increases with time (FIG. 11D). By contrast, 64 to 81% of the cells showed no response to acetylcholine (ACh), and this percentage showed no clear change with time. Even in responsive cells, the ACh-evoked currents were generally small (<20 pA). Currents elicited by glutamate showed a tendency to increase with time in culture, but evidence of a time-dependent trend was weak. In concert with the relatively large voltage gated currents was the appearance of single (FIG. 11E) and occasionally multiple action potentials (FIG. 11F) in current clamp mode. The increase in the percentage of cells that generated action potentials over time is illustrated in FIG. 11A. None of the cells showed a hyperpolarization-activated h-current characteristic of dopamine neurons. After 21 days of differentiation, spontaneous synaptic currents were detected (FIG. 11G).

Administration of tetrodotoxin did not reduce the amplitude or time course of these currents, indicating that they were spontaneous, miniature postsynaptic currents. The small amplitudes (22.6±8.4 pA) and brief decays (0.93±0.15 ms) imply that these currents were mediated by glutamate.

Example 8

Evaluation of Differentiated Stem Cells In Vivo

Stem cells have been proposed as candidates for cell replacement therapy for neurodegenerative disorders, such as PD. Both cell survival and functional integration of stem cell derived DA neurons, such as those produced by the methods described herein, may be evaluated in animal models, for example, animal models of PD.

PD can be replicated in animal models (such as mouse, rat, or non-human primate) by delivery of neurotoxins directly to the brain (for example, the substantia nigra, medial forebrain bundle, or striatum) to induce dopaminergic degeneration. Commonly used neurotoxins include 6-hydroxydopamine (6-OHDA), 1-methyl-4-phenyl-1,2,3,6-tetrahydropyridine (MPTP), rotenone, or paraquat. Genetic models of PD include rodents having altered expression of α-synuclein, parkin, or ubiquitin C-terminal hydrolase-L1.

This example describes particular methods that can be used to evaluate the survival and function of differentiated stem cells in an animal model of PD. However, one skilled in the art will appreciate that methods that deviate from these specific methods can also be used to successfully evaluate the survival and function of differentiated stem cells in a PD model.

Sprague-Dawley rats (e.g. weighing 200-300 grams) are used to generate parkinsonian rat models. Animals are divided into three groups: (i) a normal group without lesions, (ii) a sham control group with 6-OHDA lesions, and (iii) a group with 6-OHDA lesions that were transplanted with neurons derived from hESCs. 6-OHDA hydrobromide (8 mg free base in 2 ml of a solution containing 0.2% ascorbic acid; Sigma) is injected into the medial forebrain bundle for example, according to the following stereotaxic coordinates: MFB; AP −4.4 mm, ML 1.2 mm relative to bregma, and DV −7.8 mm from the dura mater. To prevent the destruction of noradrenergic neurons, desipramine (12.5 mg/kg, i.p., Sigma) is administered 30 min before the injection of 6-OHDA.

Two weeks after the development of 6-OHDA-induced lesions, the animals are tested for amphetamine-induced (3 mg/kg i.p.) and apomorphine-induced (0.1 mg/kg i.p. in saline containing AA at 2 mg/ml; Sigma) turning behavior and forepaw-adjusting stepping.

One week after behavioral testing, stem cell-derived (for example, human ESC-derived) DA neurons are transplanted into the ipsilateral striatum. Cells for transplantation are prepared with Accutase and transplanted using a sterilized stainless steel needle (0.3 mm O.D.) connected to a Hamilton microsyringe. Four microliters of the cell suspension ($1 \times 10^5$ cells per ml) is injected into the ipsilateral striatum [for example, AP; +0.2 mm, ML; 3.0 mm, DV; 4.5 mm (2 ml), and 5.5 mm (2 ml)] over a period of 4 min. Behavioral testing is conducted after the 4th, 8th, and 12th week post-transplantation. An improvement in symptoms (such as a decrease in amphetamine- or apomorphine-induced turning behavior) indicates that the transplanted dopaminergic neurons are effective for treating PD.

Twelve weeks after transplantation, the animals are anesthetized with 25% urethane in PBS and intracardially perfused with 125 ml of normal saline followed by 250 ml of ice-cold 4% paraformaldehyde in PBS. The brain of each rat is post-fixed in the same solution, cryoprotected with 30% sucrose in PBS for 48 h, and frozen. Coronal sections (thickness 10 µm) are cut on a cryostat, collected in PBS (pH 7.4), and divided into series. Brain sections are incubated overnight with primary antibodies at 4° C. The primary antibodies used for immunohistochemistry include rabbit anti-tyrosine hydroxylase (TH) (Pel-Freez), mouse anti-Msx (Developmental Studies Hybridoma Bank, University of Iowa, Iowa City, Iowa), mouse anti-human nuclei (Chemicon), and mouse anti-human mitochondria antibody (Chemicon). Fluorescent labeled secondary antibodies are used to detect the primary antibodies.

In view of the many possible embodiments to which the principles of the disclosure may be applied, it should be recognized that the illustrated embodiments are only examples and should not be considered a limitation on the scope of the invention. Rather, the scope of the invention is defined by the following claims. We therefore claim as our invention all that comes within the scope and spirit of these claims.

We claim:

1. A method of culturing stem cells to produce dopaminergic differentiated neuronal cells, comprising:
generating embryoid bodies from embryonic stem cells or induced pluripotent stem cells in the absence of fibroblast growth factor (FGF)-2; and
culturing the embryoid bodies in the presence of an effective amount of heparin, stromal cell-derived factor 1 (SDF-1), pleiotrophin (PTN), insulin-like growth factor 2 (IGF2), and ephrin B1 (EFNB 1) on an extracellular matrix for a period of time sufficient to produce differentiated neuronal cells;
thereby producing the differentiated neuronal cells.

2. The method of claim 1, wherein the extracellular matrix comprises poly-L ornithine and laminin.

3. The method of claim 1, wherein the embryoid bodies are cultured in the presence of an effective amount of heparin, SDF-1, PTN, IGF2, and EFNB1 for about 2 to about 50 days.

4. The method of claim 1, wherein the embryonic stem cells are human embryonic stem cells.

5. The method of claim 4, wherein the human embryonic stem cells are BG01, BG02 or BG03 cells, or are derived from BG01, BG02 or BG03 cells.

6. The method of claim 5, wherein the human embryonic stem cells are BG01V2 cells.

7. The method of claim 1, wherein the effective amount of SDF-1 is about 10 ng/ml to about 1,000 ng/ml SDF-1.

8. The method of claim 7, wherein the effective amount of SDF-1 is about 100 ng/ml SDF-1.

9. The method of claim 1, wherein the effective amount of PTN is about 10 ng/ml to about 1,000 ng/ml PTN.

10. The method of claim 9, wherein the effective amount of PTN is about 100 ng/ml PTN.

11. The method of claim 1, wherein the effective amount of IGF2 is about 10 ng/ml to about 1,000 ng/ml IGF2.

12. The method of claim 11, wherein the effective amount of IGF2 is about 100 ng/ml IGF2.

13. The method of claim 1, wherein the effective amount of EFNB 1 is about 20 ng/ml to about 2,000 ng/ml EFNB 1.

14. The method of claim 13, wherein the effective amount of EFNB 1 is about 200 ng/ml EFNB 1.

15. The method of claim 1, wherein the differentiated neuronal cells express tyrosine hydroxylase.

16. The method of claim 1, wherein the differentiated neuronal cells express Msx-1.

17. The method of claim 1, further comprising
administering a therapeutically effective amount of the differentiated neuronal cells to a subject having Parkinson's disease, comprising transplanting the differentiated neuronal cells in to the striatum of the subject thereby treating at least one symptom of the Parkinson's disease.

18. The method of claim 17, wherein the therapeutically effective amount comprises at least about $1 \times 10^5$ cells.

19. The method of claim 17, further comprising transplanting the differentiated neural cells into the substantia nigra or ventral tegmental area of the subject.

20. The method of claim 17, further comprising administering a therapeutically effective amount of one or more anti-Parkinson's disease agent to the subject.

21. The method of claim 20, where in the anti-Parkinson's disease agent comprises one or more of levodopa, carbidopa, dopamine agonists, catechol-O-methyltransferase inhibitors, and amantadine.

22. A method of culturing human embryonic stem cells to produce differentiated neuronal cells, comprising:
culturing BG01V2 human embryonic stem cells in low attachment plates in the absence of FGF-2 for about 4 days at about 37° C. to generate embryoid bodies; and
culturing the embryoid bodies in the presence of about 100 ng/ml stromal cell-derived factor 1 (SDF-1), about 100 ng/ml pleiotrophin (PTN), about 100 ng/ml insulin-like growth factor 2 (IGF2), about 200 ng/ml ephrin B1 (EFNB1), and about 100 μg/ml heparin on an extracellular matrix comprising poly-L-ornithine and laminin for at least about 10 days at about 37° C. to produce differentiated neuronal cells;
thereby producing the differentiated neuronal cells.

* * * * *

SEQUENCE LISTING

```
<160> NUMBER OF SEQ ID NOS: 42

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 1
gtgctgcatc gctgcttac                                                 19

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 2
acgtccctct cggacttgg                                                 19

<210> SEQ ID NO 3
<211> LENGTH: 22
<212> TYPE: DNA
```

```
<213> ORGANISM: Artificial Sequence
<220> FEATURE:
<223> OTHER INFORMATION: Synthetic oligonucleotide primer

<400> SEQUENCE: 3
atgtcgtccc agcaatatca gc                                              22

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 4
ccaagatgaa aatcaatgcc agg                                             23

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 5
tgcatcagtg acggtaaacc a                                               21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 6
ttcttcagcc gtgcaacaat c                                               21

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 7
tgtggctatg gtcgtgctg                                                  19

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 8
ccaagccctt cccacttagg                                                 20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 9
agaagcccct gcgtacattg                                                 20
```

-continued

```
<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 10
tgtccccacg atcttcatct t                                              21

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 11
ctgagcaatg agaatttcga gga                                            23

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 12
gcggtcgtct atgcctgtc                                                 19

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 13
agttggggat tcggttgttc t                                              21

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 14
cccctcattc cttaccaccc                                                20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 15
ggagcgaggc catttacaac                                                20

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide primer
```

-continued

```
<400> SEQUENCE: 16
cgtagacaag gtagcccact tt                                      22

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 17
tcttgggctg gaccatttga a                                       21

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 18
catcggtagg ggcacataga                                         20

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 19
gtaacttcgt gcctagcaac a                                       21

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 20
cctttgtcag aatactgagc agc                                     23

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 21
aactgtactg caaacaagac tacc                                    24

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 22
ttcatgtccc catcttcatc ctc                                     23

<210> SEQ ID NO 23
<211> LENGTH: 20
<212> TYPE: DNA
```

<213> ORGANISM: Artificial Sequence
<220> FEATURE:
<223> OTHER INFORMATION: Synthetic oligonucleotide primer

<400> SEQUENCE: 23
gggaccacaa catgctgctc                                       20

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 24
ccactccatt cagaaggtgc c                                     21

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 25
tcatcacctg gtcaccaagt t                                     21

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 26
ggtcgccgtg cctgtact                                         18

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 27
agggcaaccc gcccacggaa                                       20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 28
ttggtggcct ccagcggcag                                       20

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 29
ctgggtgtac tgcacacgtt at                                    22

```
<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 30
tactcgctct cgtctttgtc ct                                              22

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 31
agctgccttt gcatagctcg                                                 20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 32
agctgccttt gcatagctcg                                                 20

<210> SEQ ID NO 33
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 33
tattcactcc cgcaccaac                                                  19

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 34
agccagacat ccagaactc                                                  19

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 35
tttctcctgt ccgtcattgg c                                               21

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide primer
```

-continued

```
<400> SEQUENCE: 36
agcccacacc tttcagtatg g                                          21

<210> SEQ ID NO 37
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 37
cgacctcatc tcatttgcc                                             19

<210> SEQ ID NO 38
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 38
aatcttcatc ttccgcccc                                             19

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 39
agggaaatga tctgctggag ga                                         22

<210> SEQ ID NO 40
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 40
ctctggctgg cagttggtaa aa                                         22

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 41
accacagtcc atgccatcac                                            20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 42
tccaccaccc tgttgctgta                                            20
```